United States Patent
Wallach et al.

(10) Patent No.: US 11,885,817 B2
(45) Date of Patent: *Jan. 30, 2024

(54) BIOMARKERS AND METHODS FOR DETECTION OF SEIZURES AND EPILEPSY

(71) Applicant: EVOGEN, INC., Overland Park, KS (US)

(72) Inventors: Todd Wallach, Overland Park, KS (US); Elisa A. Waxman, Overland Park, KS (US); John Gledhill, Overland Park, KS (US); Richard St. Clair, Overland Park, KS (US); Elizabeth Brand, Overland Park, KS (US)

(73) Assignee: Cognizance Biomarkers, LLC, Miami, FL (US)

( * ) Notice: Subject to any disclaimer, the term of this patent is extended or adjusted under 35 U.S.C. 154(b) by 440 days.

This patent is subject to a terminal disclaimer.

(21) Appl. No.: 16/613,968

(22) PCT Filed: May 16, 2018

(86) PCT No.: PCT/US2018/032956
§ 371 (c)(1),
(2) Date: Nov. 15, 2019

(87) PCT Pub. No.: WO2018/213437
PCT Pub. Date: Nov. 22, 2018

(65) Prior Publication Data
US 2022/0178948 A1 Jun. 9, 2022

Related U.S. Application Data

(60) Provisional application No. 62/506,878, filed on May 16, 2017.

(51) Int. Cl.
| | | |
|---|---|---|
| *G01N 33/68* | (2006.01) | |
| *G16H 10/40* | (2018.01) | |
| *G16H 20/10* | (2018.01) | |
| *C07K 16/24* | (2006.01) | |
| *G16H 10/60* | (2018.01) | |
| *G16H 50/70* | (2018.01) | |
| *G16H 50/20* | (2018.01) | |

(52) U.S. Cl.
CPC ....... *G01N 33/6896* (2013.01); *C07K 16/244* (2013.01); *G16H 10/40* (2018.01); *G16H 20/10* (2018.01); *G01N 2333/521* (2013.01); *G01N 2333/525* (2013.01); *G01N 2333/5446* (2013.01); *G01N 2800/2857* (2013.01); *G01N 2800/52* (2013.01); *G16H 10/60* (2018.01); *G16H 50/20* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 6,346,270 B1 * | 2/2002 | Shivanand | A61K 9/0004 424/464 |
| 2005/0215770 A1 | 9/2005 | Bell et al. | |
| 2013/0331329 A1 * | 12/2013 | Pollard | A61K 38/1709 514/17.7 |
| 2014/0213926 A1 | 7/2014 | Vaidyanathan | |
| 2016/0235718 A1 | 8/2016 | Baraban | |
| 2019/0011461 A1 * | 1/2019 | Wallach | A61K 31/55 |
| 2020/0299377 A1 | 9/2020 | Wallach et al. | |

FOREIGN PATENT DOCUMENTS

| | | |
|---|---|---|
| WO | 2004051222 A2 | 6/2004 |
| WO | 2012/116264 A1 | 8/2012 |

OTHER PUBLICATIONS

Waiker et al (J Am Soc Nephrol. Jan. 2012; 23(1): 13-21) (Year: 2012).*
Mayeux (NeuroRx. Apr. 2004;1(2):182-8) (Year: 2004).*
Hegde et al (Biomarkers Med. (2014) 8(3), 413-427) (Year: 2014).*
Guido et al (Curr Med Chem. 2008;15(1):37-46) (Year: 2008).*
Franco et al (Pharmacological Research 103 (2016) 95-104) (Year: 2016).*
Goldberg (Neurotherapeutics (2021) 18:1490-1499) (Year: 2021).*
Extended European Search Report dated Aug. 4, 2021 for European Patent Application No. 18802593.6; 17 pages.
International Search Report dated Sep. 24, 2018, for International Application No. PCT/US2018/032956, 5 pages.
Written Opinion dated Sep. 24, 2018, for International Application No. PCT/US2018/032956, 12 pages.
Uludag et al. IL-1B, IL-6 and IL1Ra levels in temporal lobe epilepsy. Seizure, 2015, vol. 26, 1, 7-10, 17/1, 17/7-10, pp. 22-25. http://dx.doi.org/10.1016/j.seizure.2015.01.009.
Partial Supplementary Search Report dated May 3, 2021 for European Patent Application No. 18802593.6 ; 19 pages.

(Continued)

*Primary Examiner* — Brian Gangle
*Assistant Examiner* — Andrea K McCollum
(74) *Attorney, Agent, or Firm* — Viksnins Harris Padys Malen LLP

(57) ABSTRACT

Epileptic seizures are difficult to diagnose and are often difficult to distinguish from several conditions with similar presentations, and therefore, diagnosis of seizures is often a long, expensive, and unreliable process. This invention provides biomarkers for identifying seizures and epilepsy, assays for measuring and assessing biomarker concentration, predictive models based on biomarkers and computational systems for detecting, assessing and diagnosing phasic and tonic changes associated with seizures and epilepsy in all clinical and healthcare settings. Diagnostic and treatment methods, systems, kits, and predictive models provided herein, provide quantitative and/or qualitative assessment in order to allow patients to proceed immediately to diagnostic and/or treatment protocols, and assess therapeutic treatment effectiveness.

11 Claims, 14 Drawing Sheets

(56) References Cited

OTHER PUBLICATIONS

John R. Pollard et al: 11 The TARC/sICAM5 Ratio in Patient Plasma is a Candidate Biomarker for Drug Resistant Epilepsy 11 Frontiers in Neurology, vol. 3, No. 181, Jan. 3, 2013 (Jan. 3, 2013), pp. 1-8.
Wang Rui et al: "Evaluation of serum matrix metalloproteinase-3 as a biomarker for diagnosis of epilepsy", Journal of Neurological Sciences, Elsevier Scientific Publishing Co, Amsterdam, NL, vol. 367, Jun. 14, 2016 (Jun. 14, 2016), pp. 291-297.
Aronica, E , et al., "Gene expression profile analysis of epilepsy-associated gangliogliomas", Neuroscience 151 (1), 272-792 (2008).
Yaari, Y , et al., "Phenytoin: Mechanisms of its anticonvulsant action", Ann Neurology 20, 171-184 (1986).

\* cited by examiner

| Epileptic Seizures (ES) | Non-Epileptic Seizures (NES) | No Seizures (NS) |
|---|---|---|
| • Seizures in patients whose brains demonstrate a pathologic and enduring tendency to have recurrent seizures[1]<br><br>• Patients who have experienced at least two unprovoked seizures at least 24 hours apart<br><br>• Patients who have experienced a single unprovoked seizure and are as likely to experience additional seizures (for example, patients who have experienced a single seizure subsequent to a remote brain insult, like a stroke)<br><br>• Diagnosis of an unresolved epilepsy syndrome | • Seizures that are secondary to a transient factor<br><br>• Transient factor acting on an otherwise normal brain to temporarily lower the seizure threshold<br><br>• Examples include seizures in the context of fever or alcohol withdrawal[1] | • No seizure-like events, or events that mimic seizures<br><br>• Explained by specific medical and psychological conditions<br><br>• Examples include TIA, vertigo, panic attacks, and conversion disorder/ psychogenic spells |

[1] ILAE Official Report: A practical clinical definition of epilepsy. Epilepsia, 55(4):465-482, 2014

FIG. 1

BIOMARKERS AND METHODS FOR DETECTION OF SEIZURES AND EPILEPSY

CROSS-REFERENCE TO RELATED APPLICATIONS

This application is a National Stage Application of International Application No. PCT/US2018/032956, filed on May 16, 2018, which claims the benefit of U.S. Provisional Patent Application No. 62/506,878, filed on May 16, 2017, each of which is incorporated by reference herein in its entirety.

FIELD OF THE INVENTION

The present inventions are generally directed to biomarkers associated with inflammation and seizures, and indicate methods of characterizing biological conditions by scoring quantitative data sets derived from a subject sample, as well as various other embodiments, as described herein.

BACKGROUND OF THE INVENTION

Seizures and epilepsy are very common neurological disorders that are associated with significant morbidity, health care cost, and even mortality. Epilepsy is the fourth most common neurological disorder behind migraine, stroke, and Alzheimer's. Epilepsy is a common neurological affliction affecting over 2.3 million patients in the US and 65 million patients worldwide, with significant financial burden. Current estimates are that epilepsy affects approximately 1% of the world population. The prevalence of total active cases currently being treated for epilepsy is 17.8 million, with India (7.5 million), China (4.9 million), and the US (2.3 million) leading other countries. The financial burden of epilepsy care is substantial with a major expense contributed by tests required for appropriate diagnosis. Estimates are that epilepsy and seizures in the U.S. incurs an estimated annual cost of $17.6 billion in direct and indirect costs. A major limitation in providing care for patients with seizures is the lack of a diagnostic blood test to identify clinical events as seizures as opposed to other disorder such as transient ischemic attacks, fainting, sleep disorders, and psychogenic events.

Epilepsy, defined by spontaneous and recurrent seizures, is a highly prevalent public health problem. Also known as "seizure disorder," epilepsy is not diagnosed until after the patient has had two seizures not caused by a known medical condition. In 70% of new cases, no cause is apparent. Approximately, 30-50% of people who have had a single, unprovoked seizure will develop recurrent seizures (epilepsy). One-third of people with epilepsy live with uncontrolled seizures because no available treatment works for them.

While much research has been devoted to developing new anti-epileptic drugs (AEDs), the "gold standard" diagnostic protocol—which often hinges on EEGs—has remained constant and inadequate. When patients present with a suspected seizure, the process to diagnose whether the event was caused by epilepsy or another disorder is most often long and expensive. Patients undergo a lengthy work-up that regularly includes blood tests, imaging studies, EEGs, and video EEGs where available. Often the diagnosis is one of exclusion where other medical conditions are "ruled-out;" and definitive diagnosis of epilepsy is typically made if an EEG records an epileptic seizure "event" while it is occurring, usually during a lengthy and expensive stay in an in-patient epilepsy monitoring unit.

In addition to the high cost associated with a long engagement with the health system, the current state of epilepsy diagnosis presents another critical issue: in the absence of a good triage tool for early diagnosis, patients who experience suspected seizures because of other underlying conditions may be either over- or under-treated erroneously with AEDs, during which time their underlying conditions remain untreated, while patients experience undesirable side-effects from unnecessary medications. Thus, timely diagnosis of the patient's condition (whether epilepsy or not) remains a significant unmet medical need.

SUMMARY OF THE INVENTION

In an embodiment, the invention "EvoScore™" includes a blood based diagnostic test, that effectively screens plasma from patients to identify measurable changes in select proteins following seizures. Multiple proteins linked to inflammatory processes are used to generate, a predictive algorithm with associated score (EvoScore Predictive Models™) that can be translated into a diagnostic test for seizures. The algorithms, which combine protein levels has demonstrated, with strong diagnostic performance, predictions of both phasic and tonic changes (acute and chronic) in patients with seizures and epilepsy—both ruling out patients and ruling in patients with seizures and epilepsy, with the ability to monitor patients over time and over the course of treatment. EvoScore can be used in all clinical and healthcare settings, including direct use by a patient. The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy patients, drug controlled epilepsy patients and drug refractory patients. The test score and biomarkers can be analyzed and compared across patients, patient groups, other indications and normal controls, and across an individual patient over time for personalized medicine.

In an embodiment, the invention includes a method for diagnosing epilepsy and/or a seizure in a mammalian subject. In some embodiments, the method may include the step of contacting a blood plasma or blood serum sample obtained from the mammalian subject with a diagnostic reagent that can measure or detect the expression of one biomarker. In some embodiments, the method may include the step of contacting said blood plasma or blood serum sample obtained from the mammalian subject with a diagnostic reagent that can measure or detect the expression level of one biomarker and developing a diagnostic algorithm. In some embodiments, the method may include the step of contacting a blood plasma or blood serum sample obtained from the mammalian subject with a diagnostic reagent that can measure or detect the expression of two biomarkers. In some embodiments, the method may include the step of contacting said blood plasma or blood serum sample obtained from the mammalian subject with a diagnostic reagent that can measure or detect the expression level of two biomarkers and developing a diagnostic algorithm. In some embodiments, the method may include the step of contacting a blood plasma or blood serum sample obtained from the mammalian subject with a diagnostic reagent that can measure or detect the expression of three biomarkers. In some embodiments, the method may include the step of contacting said blood plasma or blood serum sample obtained from the mammalian subject with a diagnostic reagent that can measure or detect the expression level of three biomarkers and developing a diagnostic algorithm. In some embodiments, the method may include the step of contacting a blood plasma or blood serum sample obtained from the mammalian subject with a diagnostic reagent that can measure or detect the expression of three or more biomarkers. In some embodiments, the method may include the step of contacting said blood plasma or blood serum sample obtained from the mammalian subject with a diagnostic reagent that can measure or detect the expression level of three or more biomarkers and developing a diagnostic algorithm. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the subject is a human subject.

In one embodiment, the invention includes a method for treating epilepsy in a patient, the method including: (a) contacting a blood sample obtained from said patient with an antibody targeting IL-16; (b) measuring the concentration of IL-16 in said sample; (c) comparing the concentration of IL-16 in said sample to the concentration of IL-16 in a control; (d) wherein said patient has epilepsy when the concentrations of IL-16 is altered in said sample relative to control; and (e) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method for treating epilepsy in a patient, the method including: (a) contacting a blood sample obtained from said patient with an antibody targeting TARC; (b) contacting said sample with an antibody targeting IL16, (c) measuring the concentration of TARC in said sample; (d) measuring the concentration of IL-16 in said sample; (e) comparing the concentration of TARC in said sample to the concentration of TARC in a control; (f) comparing the concentration of IL-16 in said sample to the concentration of IL-16 in a control; (g) wherein said patient has epilepsy when the concentrations of TARC and IL-16 is elevated in said sample relative to control; and (h) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method for treating epilepsy in a patient comprising targeting two biomarkers selected from Table 2, the method including: (a) contacting a blood sample obtained from said patient with an antibody targeting biomarker 1; (b) contacting said sample with an antibody targeting biomarker 2; (c) measuring the concentration of biomarker 1 in said sample; (d) measuring the concentration of biomarker 2 in said sample; (e) comparing the concentration of biomarker 1 in said sample to the concentration of biomarker 1 in a control; (f) comparing the concentration of biomarker 2 in said sample to the concentration of biomarker 2 in a control; (g) wherein said patient has epilepsy when the concentrations of biomarker 1 and biomarker 2 is elevated in said sample relative to control; and (h) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method for treating epilepsy in a patient comprising targeting three biomarkers selected from Table 2, the method including: (a) contacting a blood sample obtained from said patient with an antibody targeting biomarker 1; (b) contacting said sample with an antibody targeting biomarker 2; (c) contacting said sample with an antibody targeting biomarker 3; (d) measuring the concentration of biomarker 1 in said sample; (e) measuring the concentration of biomarker 2 in said sample; (f) measuring the concentration of biomarker 3 in said sample; (g) comparing the concentration of biomarker 1 in said sample to the concentration of biomarker 1 in a control; (h) comparing the concentration of biomarker 2 in said sample to the concentration of biomarker 2 in a control; (i) comparing the concentration of biomarker 3 in said sample to the concentration of biomarker 3 in a control; (j) wherein said patient has epilepsy when the concentrations of biomarker 1, biomarker 2 and biomarker 3 is elevated in said sample relative to control; and (k) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method for treating epilepsy in a patient comprising targeting three or more biomarkers selected from Table 2, the method including: (a) contacting a blood sample obtained from said patient with an antibody targeting biomarkers; (b) measuring the concentration of biomarkers in said sample; (c) comparing the concentration of biomarkers in said sample to the concentration of biomarkers in a control; (d) wherein said patient has epilepsy when the concentrations of biomarkers are elevated in said sample relative to control; and (e) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method for treating epilepsy in a patient comprising targeting three biomarkers selected from Table 2, the method including: (a) contacting a blood sample obtained from said patient with an antibody targeting TARC; (b) contacting said sample with an antibody targeting IL-16; (c) contacting said sample with an antibody targeting biomarker TNF-alpha; (d) measuring the concentration of TARC in said sample; (e) measuring the concentration of IL-16 in said sample; (f) measuring the concentration of TNF-alpha in said sample; (g) comparing the concentration of TARC in said sample to the concentration of TARC in a control; (h) comparing the concentration of IL-16 in said sample to the concentration of IL-16 in a control; (i) comparing the concentration of TNF-alpha in said sample to the concentration of TNF-alpha in a control; (j) wherein said patient has epilepsy when the concentrations of TARC, IL-16 and TNF-alpha is elevated in said sample relative to control; and (k) treating said patient for epilepsy. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method of treating epilepsy in a patient in need of epilepsy treatment, the method comprising: contacting one or more blood samples obtained from the patient with one or more antibodies targeting one or more biomarkers selected from Table 2; measuring the concentrations of the one or more biomarkers in the one or more blood samples; comparing the concentrations of the one or more biomarkers in the one or more blood samples to the concentration of the one or more biomarkers in one or more controls; and treating the patient for epilepsy; wherein the patient is in need of epilepsy treatment when the concentrations of the one or more biomarkers are elevated in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method of predicting whether a subject will have a seizure, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is predicted to have a seizure when the concentrations of the one or more biomarkers are elevated in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has already suffered one or more seizures. In some embodiments, the subject has already suffered one seizure. In some embodiments, the subject has already suffered two seizures. In some embodiments, the subject is a human subject.

In one embodiment, the invention includes a method of predicting whether a subject needs treatment including a therapeutic agent effective to treat seizures, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is predicted to need treatment including a therapeutic agent effective to treat epileptic seizures when the concentrations of the one or more biomarkers are elevated in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures. In some embodiments, the subject has suffered one seizure. In some embodiments, the subject has suffered two seizures. In some embodiments, the subject is a human subject. In some embodiments, a therapeutic agent effective to treat epileptic seizures includes one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof.

In one embodiment, the invention includes a method of selecting a therapeutic agent effective to treat epileptic seizures in a subject, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the ratio(s) of the concentrations of the one or more biomarkers from the one or more blood samples relative to the one or more controls is predictive of the effectiveness of a specific therapeutic agent. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures. In some embodiments, the subject has suffered one seizure. In some embodiments, the subject has suffered two seizures. In some embodiments, the subject is a human subject. In some embodiments, a therapeutic agent effective to treat epileptic seizures includes one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof.

In one embodiment, the invention includes a method of adjusting the dose of a therapeutic agent effective to treat epileptic seizures in a subject, the method comprising: contacting one or more blood samples obtained from the subject with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the ratio(s) of the concentrations of the one or more biomarkers from the one or more blood samples relative to the one or more controls is predictive of a need to adjust the dose of the therapeutic agent. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the subject has suffered one or more seizures. In some embodiments, the subject has suffered one seizure. In some embodiments, the subject has suffered two seizures. In some embodiments, the subject is a human subject. In some embodiments, a therapeutic agent effective to treat epileptic seizures includes one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof.

In some embodiments, a method of treating epilepsy in a patient includes administering to the patient one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method of treating epilepsy in a patient likely to benefit from epilepsy treatment, the method including administering to the patient one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the likelihood of beneficial epilepsy treatment is determined by a serum based analytical method including the steps of: contacting one or more blood samples obtained from the patient with one or more antibodies targeting one or more biomarkers selected from Table 2; measuring the concentrations of the one or more biomarkers in the one or more blood samples; and comparing the concentrations of the one or more biomarkers in the one or more blood samples to the concentration of the one or more biomarkers in one or more controls; wherein the patient is likely to benefit from epilepsy treatment when the concentrations of the one or more biomarkers are elevated in the one or more blood samples relative to the one or more controls. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a method of treating epilepsy in a patient having an elevated blood level of one or more biomarkers selected from Table 2, the method including administering to the patient one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the elevated blood level of the one or more biomarkers is determined by a serum based analytical method including the steps of: contacting one or more blood samples obtained from the patient with one or more antibodies targeting the one or more biomarkers; measuring the concentrations of the one or more biomarkers in the one or more blood samples; and comparing the concentrations of the one or more biomarkers in the one or more blood samples to the concentration of the one or more biomarkers in one or more controls. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the one biomarker is IL-16. In some embodiments, the one biomarker is TARC. In some embodiments, the one biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the patient has suffered one or more seizures. In some embodiments, the patient has suffered one seizure. In some embodiments, the patient has suffered two seizures. In some embodiments, the patient is a human subject.

In one embodiment, the invention includes a system for determining a likelihood that a subject will be responsive to a treatment regimen that includes administering to the subject an epilepsy therapeutic agent, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy to the subject or to a practitioner charged with caring for the subject. In some embodiments, elevated concentrations of the one or more biomarkers in the one or more blood samples compared to the concentration of the one or more biomarkers in the one or more controls indicate a positive likelihood that the subject will be responsive to the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject.

In one embodiment, the invention includes a system for predicting a likelihood that a subject will have a seizure, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions to the subject or to a practitioner charged with caring for the subject that the subject is likely to have a seizure. In some embodiments, elevated concentrations of the one or more biomarkers in the one or more blood samples compared to the concentration of the one or more biomarkers in the one or more controls indicate that the subject will have a seizure. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject.

In one embodiment, the invention includes a system for determining a likelihood that a subject needs a treatment regimen that includes administering to the subject an epilepsy therapeutic agent, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy to the subject or to a practitioner charged with caring for the subject. In some embodiments, elevated concentrations of the one or more biomarkers in the one or more blood samples compared to the concentration of the one or more biomarkers in the one or more controls indicate that the subject needs the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject.

In one embodiment, the invention includes a system for selecting a specific therapeutic agent for a treatment regimen in a subject, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for selecting a specific therapeutic agent to the subject or to a practitioner charged with caring for the subject. In some embodiments, elevated concentrations of the one or more biomarkers in the one or more blood samples compared to the concentration of the one or more biomarkers in the one or more controls indicate that the subject needs a specific therapeutic agent. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject.

In one embodiment, the invention includes a system for adjusting the dosage of a therapeutic agent for a treatment regimen in a subject, the system including: memory; one or more processors; and one or more modules stored in memory and configured for execution by the one or more processors, the modules comprising instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for adjusting dosage of the therapeutic agent to the subject or to a practitioner charged with caring for the subject. In some embodiments, elevated concentrations of the one or more biomarkers in the one or more blood samples compared to the concentration of the one or more biomarkers in the one or more controls indicate that the dosage of the therapeutic agent needs to be adjusted. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha.

In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximede, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject.

In one embodiment, the invention includes a non-transitory computer readable storage medium for determining a likelihood that a subject will be responsive to a treatment regimen that includes administering to the subject an epilepsy therapeutic agent, the non-transitory computer readable storage medium storing one or more programs for execution by one or more processors of a computer system, the one or more computer programs including instructions for: (a) obtaining the concentration of one or more biomarkers in a blood sample obtained from the subject by contacting the blood sample with one or more antibodies targeting the one or more biomarkers; (b) comparing the concentrations of the one or more biomarkers in the one or more blood samples to the concentration of the one or more biomarkers in one or more controls; and (c) providing instructions for treating the subject for epilepsy to the subject or to a practitioner charged with caring for the subject. In some embodiments, elevated concentrations of the one or more biomarkers in the one or more blood samples compared to the concentration of the one or more biomarkers in the one or more controls indicate a positive likelihood that the subject will be responsive to the treatment regimen. In some embodiments, the one or more biomarkers are selected from Table 2. In some embodiments, the one or more biomarkers are selected from the group consisting of one biomarker, two biomarkers, and three biomarkers. In some embodiments, the one or more biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuxemide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject is a human subject. The invention also includes non-transitory computer readable storage mediums for determining likelihoods as described herein, as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past.

In some embodiments, the method may include the step of contacting said blood plasma or blood serum sample obtained from the mammalian subject with a diagnostic reagent that can measure or detect the expression level of IL-16. In some embodiments, the method may include the step of comparing the concentrations of IL-16 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TARC. In some embodiments, the method may include the step of comparing the concentrations of TARC to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TRAIL. In some embodiments, the method may include the step of comparing the concentrations of TRAIL to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-4. In some embodiments, the method may include the step of comparing the concentrations of MCP-4 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of IL-7. In some embodiments, the method may include the step of comparing the concentrations of IL-7 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of P-Cadherin. In some embodiments, the method may include the step of comparing the concentrations of P-Cadherin to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of Osteoactivin. In some embodiments, the method may include the step of comparing the concentrations of Osteoactivin to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of ICAM-1. In some embodiments, the method may include the step of comparing the concentrations of ICAM-1 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MMP-3. In some embodiments, the method may include the step of comparing the concentrations of MMP-3 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of M-CSF. In some embodiments, the method may include the step of comparing the concentrations of M-CSF to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-2. In some embodiments, the method may include the step of comparing the concentrations of MCP-2 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of GM-CSF. In some embodiments, the method may include the step of comparing the concentrations of GM-CSF to normal control concentrations. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MCP-1. In some embodiments, the method may include the step of comparing the concentrations of MCP-1 to normal control concentrations. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of VCAM-1. In some embodiments, the method may include the step of comparing the concentrations of VCAM-1 to normal control concentrations. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of MIP-1β. In some embodiments, the method may include the step of comparing the concentrations of MIP-1β to normal control concentrations. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of TNF-α. In some embodiments, the method may include the step of comparing the concentrations of TNF-α to normal control concentrations. In some embodiments, the method may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of IL-8. In some embodiments, the method may include the step of comparing the concentrations of IL-8 to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of SAA. In some embodiments, the method may include the step of comparing the concentrations of SAA to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of other markers defined herein. In some embodiments, the method may include the step of comparing the concentrations of other markers defined herein to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In some embodiments, the method may include the step of contacting said blood plasma or blood serum sample obtained from the mammalian subject with a diagnostic reagent that can measure or detect the expression level of CRP. In some embodiments, the method may include the step of comparing the concentrations of CRP to normal control concentrations. In some embodiments, the method may include the step of diagnosing epilepsy in the mammalian subject. In some embodiments, it may be combined with one or more biomarkers as defined herein, and may be incorporated into a diagnostic algorithm. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In an embodiment, the invention includes a method for diagnosing epilepsy and/or a seizure in a mammalian subject that may include the step of contacting a blood plasma or blood serum sample obtained from the mammalian subject with a diagnostic reagent that can measure or detect the expression level of TARC. In some embodiments, the method may include the step of contacting said blood plasma or blood serum sample obtained from the mammalian subject with a diagnostic reagent that can measure or detect the expression level of IL-16. In some embodiments, the method may include the step of comparing the concentrations of TARC and IL-16 to normal control concentrations. In some embodiments, the method may include the step of comparing concentration ratios of TARC and IL-16 to normal control concentration ratios. In some embodiments, the measurements can be performed in multiple locations, including but not limited to, direct by the patient, at the point of care, in a physician's office or performed in a laboratory, which may include the step of diagnosing epilepsy in the mammalian subject. The method may also include administering a therapy for seizure and or epilepsy to the patient. Measurements can be performed in multiple locations, including but not limited to, direct by the patient, at the point of care, in a physician's office or performed in a laboratory. In some embodiments, the mammalian subject is a human subject.

In an embodiment, the invention includes a kit for generating quantitative data for a patient. In some embodiments, the kit may include a diagnostic reagent that can measure an expression level of IL-16 in a blood plasma or blood serum sample taken from the patient. In some embodiments, the kit may include a diagnostic reagent that can measure an expression level of TARC in the blood plasma or blood serum sample taken from the patient. In some embodiments, the kit may include a diagnostic reagent that can measure an expression level of TNF-α in the blood plasma or blood serum sample taken from the patient. In some embodiments, the kit may include an analysis unit for comparison of the expression levels of IL-16, TARC, and TNF-α to expression levels of normal controls. In some embodiments, the kit may include an analysis unit for comparison of the expression levels of IL-16, TARC, and TNF-α and any one or more biomarkers contained and defined herein, including but not limited to IL-1B, IL-2, IL-6, IL-8, IL-10, IL-12p70, IFN-γ, IL-13, IL-4, IL-17A, GM-CSF, IL-12/IL-23p40, IL-15, IL-1α, IL-5, IL-7, TNFβ, VEGF-A, MCP-1/CCL2, Eotaxin, Eotaxin-3, IP-10, MCP-4, MDC, MIP-1α, MIP-1β, sICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL such as to expression levels of normal controls. The method may also include administering a therapy for seizure and or epilepsy to the patient. Measurements can be performed in multiple locations, including but not limited to, direct by the patient, at the point of care, in a physician's office or performed in a laboratory. In some embodiments, the patient is a human subject.

In an embodiment, the invention includes a system for scoring a sample, said system comparing expression levels of one or more biomarkers to determine epilepsy from normal controls. The method may also include administering a therapy for seizure and or epilepsy to the patient. Measurements can be performed in multiple locations, including but not limited to, direct by the patient, at the point of care, in a physician's office or performed in a laboratory. In some embodiments, the patient is a human subject.

In an embodiment, the invention includes a computer having software, with said software comparing expression levels of one or more biomarkers to determine epilepsy from normal controls. The method may also include administering a therapy for seizure and or epilepsy to the patient. Measurements can be performed in multiple locations, including but not limited to, direct by the patient, at the point of care, in a physician's office or performed in a laboratory. In some embodiments, the patient is a human subject.

In an embodiment, the invention includes a method of treating a seizure disorder in a patient with altered blood plasma or blood serum expression levels of one or more biomarkers, a product of or a ratio of a combination thereof, relative to a normal control, the method including administering a therapy for epilepsy to the patient. Measurements can be performed in multiple locations, including but not limited to, direct by the patient, at the point of care, in a physician's office or performed in a laboratory.

BRIEF DESCRIPTION OF THE DRAWINGS

The foregoing summary, as well as the following detailed description of the invention, will be better understood when read in conjunction with the appended drawings.

FIG. 1 illustrates criteria for different types of seizures.

DETAILED DESCRIPTION OF THE INVENTION

Figure 2:
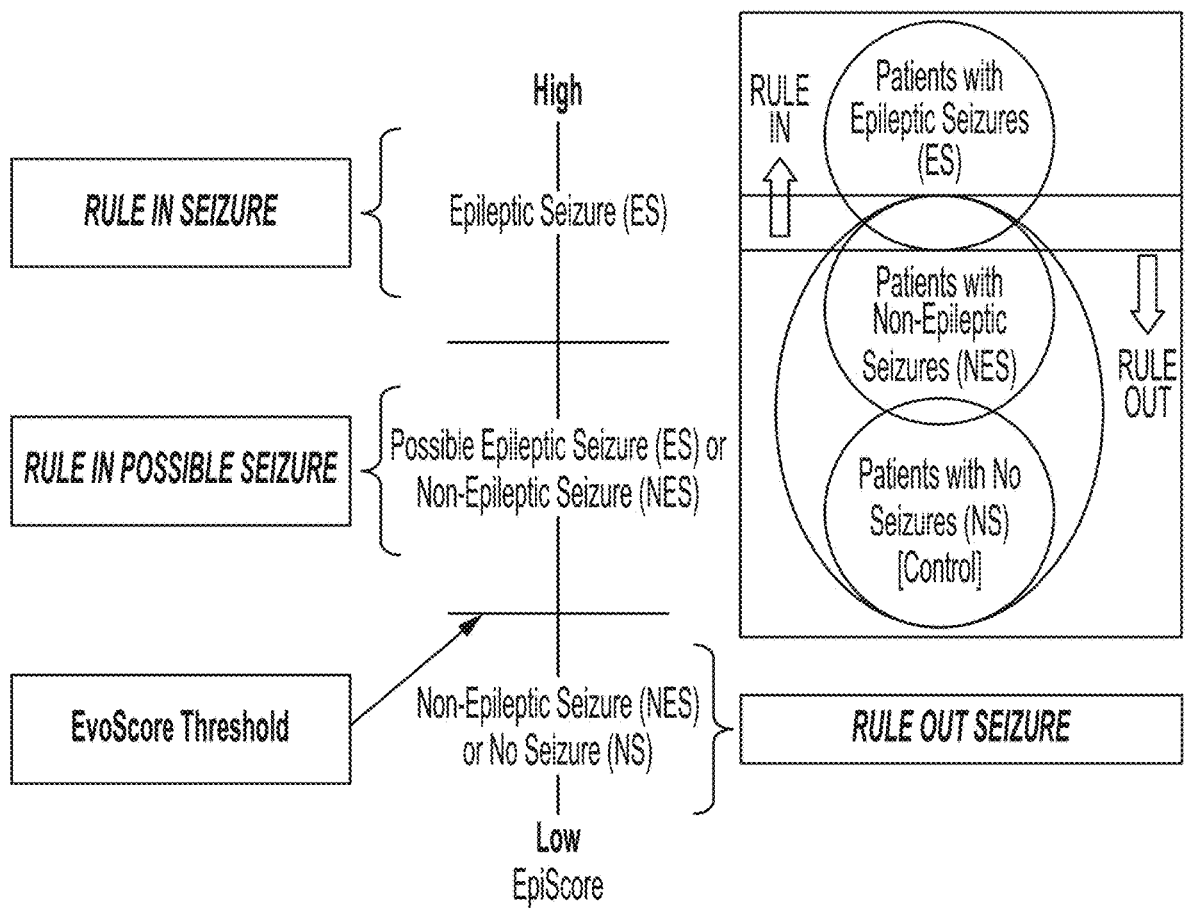
FIG. 2 illustrates the objectives of the algorithm and ultimate actionable results.

Epileptic seizures are difficult to diagnose and are often difficult to distinguish from several conditions with similar presentations, and therefore, diagnosis of seizures is often a long, expensive, and unreliable process. Predictive Models (EvoScore™) give clinicians the ability to quickly triage patients by ruling out epilepsy. Predictive Models will allow patients to proceed immediately to diagnostic protocols that are most likely to result in effective treatment, saving significant time and money and sparing patients from unnecessary tests.

This application is directed towards a blood test for seizure and epilepsy diagnosis and etiology classification in all clinical settings. In some embodiments, individual and panels/arrays of biomarkers indicative of seizure or a tendency to have seizure are provided, including methods for detecting seizure, methods for assessing the effectiveness of a treatment of seizure, a tendency to have seizure or treatment of any underlying disorder resulting in seizure, and diagnostic kits. In other embodiments, Predictive Models are provided, providing both quantitative and qualitative scores predicting phasic and tonic changes associated with seizures and epilepsy. The score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative."

Epilepsy Diagnostic Methodologies

Accurately diagnosing epilepsy is very challenging and time consuming because clinicians rarely observe the actual seizure, plus there are many different types of seizures and epilepsy syndromes with differing presentations. Furthermore, other neurological disorders can be mimics for seizures leading to erroneous diagnosis, inappropriate treatments with significant potential adverse events, incorrect prognosis, and significant waste of health care resources. Clinical events such as movement disorders e.g., tremors, tics, dyskinesias, fainting spells/syncope, transient ischemic attacks (TIA), sleep disorders/parasomnias, and somatiform psychiatric disorders can be mistaken for seizures even by seasoned clinicians. Rendering a definitive diagnosis of seizures is critical to long-term patient health and outcome that will lead to early treatment, subsequent follow up and surveillance, counseling, and support. Currently, obtaining a definitive diagnosis of seizures or epilepsy is expensive and inconvenient for patients as it may require inpatient evaluation and a battery of costly tests. The diagnosis of epilepsy has for years relied on a broad costly and often cumbersome medical-neurological evaluation that includes:

The "gold standard" test is electroencephalography (EEG). If a seizure is captured during the recording, seizure activity will appear as rapid spiking waves on the EEG. Brain lesions, i.e., tumors, strokes, may cause slowing of normal electrical brain rhythms. The challenge with EEG is that it is typically performed as a post hoc assay, that is, after the clinical event is finished, and may in fact be normal. A continuous EEG is a 24 hour EEG done in the hospital to get a prolonged pattern and try to "catch" the seizure when occurring. This requires a costly inpatient hospital stay, and there is no way to know for certain that a clinical event will occur during the stay. Obviously, this provides a significant logistical challenge to caregivers in the outpatient and emergency department (ED) settings since most patients come to the ED after the event has ended and only historical information is gathered; definitive diagnosis of a single seizure is essentially impossible and empiric at best. EEG is only about at best 30 to 50% sensitive (measures proportion of positives that are correctly identified).

Medical History to determine circumstances surrounding first seizure like event, the duration and frequency of the event, and age of onset. Often the patients or caregivers cannot give the level of detail needed for accurate diagnosis. Missing information regularly includes time of onset and duration of event due to the fact that a caregiver was either not present or failed to keep accurate records. Seizure-like events are traumatic events for patients, caregivers, and responders where the first reaction is to care for the patient and not to keep track of timing or other information necessary for diagnosis.

Laboratory studies including complete blood count (CBC), chemistry metabolic panel (CMP), and toxicology screen tests. These do not diagnose the "seizure" itself, but instead may provide clues to explain neurological dysfunction. Measurement of prolactin levels is unreliable. EEG is used to evaluate several types of brain disorders.

MRI is a technique used to create an image or scan of the brain. MRI scans can be used examine a person's brain structure. An MRI scan cannot, by itself, determine whether the person has epilepsy, but when considered with other information, may help the clinician decide if epilepsy is a likely cause of the seizure like events.

PET scan may be used to locate the part of the brain causing seizure like events as it gives clinicians additional information about how the cells in the body are functioning. While PET scans are helpful in some cases, they often show abnormalities that are not related to epilepsy and are less often part of the diagnostic process.

Lumbar puncture is a procedure in which fluid surrounding the spinal cord is withdrawn through needle aspiration and analyzed in the lab. It is performed to rule out infections, such as meningitis or encephalitis, as the cause of seizure like events.

Timely Diagnosis: An Unmet Need

The diagnostic process can take several months before clinical events are pinpointed as epileptic seizures, and often clinical care is largely empiric, based on supporting but not definitive evidence—often resulting in either under- or over-diagnosis and treatment. Thus, timely and accurate seizure diagnosis remains an unmet medical need. Not only is the diagnostic process long, there is a significant burden on the healthcare system with annual figures for epilepsy diagnostic methodologies totaling greater than $15 billion in the US alone. Thus, a critical gap in our clinical assessment of seizures in virtually every clinical setting is an accurate diagnostic blood test for seizures that can be used for either single or recurrent events to identify both phasic and tonic changes in brain activity. Numerous clinical scenarios can be envisioned in which a clinical diagnostic test for seizures would be invaluable to explain a patient's clinical condition: 1) an individual is brought to the ED after collapsing at home; 2) an individual is found confused and wandering in the street; 3) a hospitalized patient has a brief episode of unresponsiveness or change in mental status; 4) patients in third world countries where EEG, CT, or MRI are not readily available. A simple blood test that could provide immediate and definitive explanation of the clinical event with actionable results would be an enormous diagnostic advance and could direct further studies towards ("rule in") or away ("rule out") from epilepsy, saving resources, time, and expense. In short, a simple blood test for seizures would be a major innovation.

Accurately diagnosing epilepsy is very challenging and time consuming because clinicians rarely observe seizures and there are many different types of seizures and epilepsy syndromes with differing presentations. The diagnosis of epilepsy has for years relied on a "gold standard" to include patient medical history (inclusive of complete blood count and chemistry metabolic profile) and electroencephalograph (EEG). Once these are analyzed, the clinician may also perform magnetic resonance imaging (MRI) and continuous video EEG (vEEG) where available. Additional diagnostic techniques may include positron emission tomography (PET) scan and lumbar puncture (spinal tap). A major challenge in the diagnosis of epilepsy using the gold standard EEG is the fact that EEG has a low sensitivity for epilepsy, ranging between 25-56%. Specificity is better, but also variable at 78-98% —as specificity is dependent on the skill of the physician reading the EEG. Additionally, while often adequate for the appropriate diagnosis of a seizure disorder, EEGs can appear persistently normal for patients with epilepsy. In fact, in our studies, EEG was demonstrated to have a Sensitivity of 37-55%, Specificity of 98-99%, PPV of 98%, and NPV of 64-66%, which validates the need for a test that maximizes sensitivity when diagnosing a seizure.

Importantly, while patients are undergoing months of diagnostic work-up for epilepsy, as described above, they are typically subjected to a period of AED medication trial and error to determine which—if any—medications control their seizures. Especially when considering the side-effect-laden and in some cases teratogenic consequences of AEDs, this unnecessary medication cost is huge and when combined with the long diagnostic process, there is a significant burden on the health care system with annual figures for epilepsy diagnostic methodologies totaling greater than $15 billion in the US alone.

In an effort to streamline epilepsy diagnosis, it has been observed that prolactin levels were elevated subsequent to a seizure. Further clinical evaluation of application of prolactin for seizure diagnosis indicated that prolactin is only a viable biomarker for seizure if a sample is collected within 10 and 20 minutes of a seizure. Additionally, Prolactin is only applicable to a subset of seizures including primary or secondarily generalized tonic-clonic seizures and partial complex seizures of temporal lobe origin. Accordingly, the short window of viability (minutes after), coupled with inadequate diagnostic sensitivity, specificity, and accuracy, preclude prolactin from being a practical seizure biomarker, and is rarely, if ever used today in clinical settings.

Link Between Inflammation and Seizures

Seizures induce an inflammatory response in brain tissue where the seizure starts. For example, there may be a robust inflammatory response in the resected brain specimens of intractable epilepsy patients including expression of critical proinflammatory cytokines and chemokines such as tumor necrosis factor alpha (TNFα, interleukin-8 (IL-8), interleukin-6 (IL-6), and interferon gamma (IFNγ). Increased levels of TNFα, IL-8, IL-6, and IFNγ have also been detected in mouse seizure models highlighting the idea that inflammatory processes in the brain contribute to the pathogenesis of seizures and to the establishment of a chronic epileptic focus. Many of these cytokines have been detected in the cerebrospinal fluid of seizure patients immediately following seizures as well. Expression of several cytokine receptor subtypes is also upregulated on neurons and astrocytes, suggesting a mechanism for activated intracellular signaling, highlighting autocrine and paracrine actions of cytokines in the brain. Functional interactions between cytokines and classical neurotransmitters such as glutamate and GABA suggest the possibility that these interactions underlie established cytokine-mediated changes in neuronal excitability, thus promoting seizures. There is also clear evidence that acute seizures can induce increased blood-brain barrier permeability. The effect has been shown to facilitate passage of activated T-cells and macrophages into brain tissue, facilitating an inflammatory response in the brain, and fostering the leakage of brain specific inflammatory cytokines and chemokines into peripheral blood.

TARC (Thymus and activation-regulated chemokine; CCL17) is a chemokine (i.e., cytokine that is responsible for the movement of T and B lymphocytes, monocytes, neutrophils, eosinophils and basophils, in allergic and other inflammatory conditions) that principally expressed in the thymus and blood mononuclear cells. TARC functions as a proinflammatory cytokine and lymphocyte chemoattractor that binds specifically to CCR4 receptors on T-cells and induces chemotaxis in T-cell lines. Since TARC binds to CCR4, it is considered a Th2 type chemokine. TARC is produced by multiple cell types including dendritic cells, endothelial cells, keratinocytes and fibroblasts. Serum TARC levels have been shown to be a useful assay for disease activity in atopic dermatitis, an inflammatory disorder of the skin affecting children and adults. Indeed, TARC is an established systemic rheostat for inflammation. TARC exhibits low-level expression in the choroid plexus in the brain but has minimal expression by neurons or astrocytes. However, little is known about changes in plasma TARC expression as a consequence of seizures.

TNF-α is a secreted cytokine that has been implicated in a range of neurological disorders including stroke, Alzheimer's disease, cancer, and autism. A number of studies have examined TNFα levels in both experimental epilepsy model systems as well as human samples including CSF and serum. Kainate induced seizures in the rat induce TNF-α expression in hippocampus. In dogs with spontaneous seizures, TNF-α levels are elevated in CSF and manipulation of TNF-α signaling cascades in mouse seizure models can attenuate seizure. TNF-α levels are robustly elevated in patients with temporal lobe epilepsy suggesting it is a broad marker of inflammation in the brain, especially in the setting of seizures.

Interleukin (IL)-16, also known as lymphocyte chemoattractant factor, is a pro-inflammatory cytokine produced by a variety of immune (T cells, eosinophils, and dendritic cells) and non-immune (fibroblasts, epithelial, and neuronal) cells. IL-16 can be produced in a precursor (pro) form that is cleaved by caspase-3 and then secreted as IL-16 and interacts with its receptor, CD4. IL-16 acts as an immunomodulator, contributing to CD4+ cell recruitment and activation at sites of inflammation. IL-16 has been associated with asthma, inflammatory bowel disease, cancer, and autoimmune diseases, including multiple sclerosis. In the brain, IL-16 can be produced in neurons as a different pro-form, NIL-16, or by microglia, and can interact with CD4 expressed on neurons or microglia. IL-16 levels are reported to correlate with seizure time during electroconvulsive therapy for depression, and IL-16 positive microglia have also been shown to accumulate in the brain after focal cerebral infarctions. Prior to the current work, IL-16 had not been directly investigated in relationship to epilepsy.

Serum amyloid A (SAA) is a family of homologous apolipoproteins that respond to acute inflammation and bind to high-density lipoprotein (HDL). SAA is produced predominantly in the liver in response to inflammatory cytokines, such as IL-1β, IL-6, and TNF-α. SAA has been implicated in several pathological conditions including atherosclerosis, rheumatoid arthritis, Alzheimer's disease, and cancer. Increases in SAA levels have been previously noted after brain injury and epilepsy.

Tumor necrosis factor-related apoptosis-inducing ligand (TRAIL), also known as Apo2L and TNFSF10 (tumor necrosis factor ligand superfamily 10), is a cytokine that produces apoptotic cell death through binding to death receptors and activating caspase-8, NF-κB, and BID. The major known function of TRAIL is in tumor defense and protection against malignancies. TRAIL may also mediate cell death in a variety of other cell types and has been implicated in cell death associated with Alzheimer's disease and Multiple Sclerosis. Increased TRAIL expression has been identified in brain tissue of patients with epilepsy.

Monocyte chemotactic protein (MCP)-4, also known as chemokine (C-C motif) ligand (CCL)-13, is a potent chemoattractant for eosinophils, monocytes, lymphocytes, and basophils. MCP-4 binds to chemokine receptors, through which it recruits leukocytes to inflamed tissues. MCP-4 has been mainly implicated in inflammatory diseases such as asthma, rheumatoid arthritis, and chronic obstructive pulmonary disease. No association with epilepsy or neuronal injury has previously been identified.

Intercellular adhesion molecule (ICAM)-1 is a cell surface glycoprotein structurally related to immunoglobulins. ICAM-1 expression is upregulated in response to inflammation, resulting in T-cell proliferation and cytokine release. ICAM-1 is also involved in angiogenesis, wound healing, and bone metabolism. Soluble forms of ICAM-1 (sICAM-1) can be generated through proteolytic cleavage. Elevated levels of sICAM-1 are associated with cardiovascular disease, type 2 diabetes, rheumatoid arthritis, and certain cancers. Reduced sICAM-1 has been previously observed in schizophrenic patients. In a separate study, sICAM levels were noted to be higher in epileptic patients than neurotic controls.

Matrix Metalloproteinase (MMP)-3 is a proteolytic enzyme involved in remodeling of the extracellular matrix. MMP-3's major function is in tissue injury and repair. MMP-3 has been implicated in arthritis, arthrosclerosis, fibrosis, neurodegeneration, and cancer. A previous study found MMP-3 levels decreased in epilepsy patients versus controls.

Macrophage inflammatory protein (MIP)-1β, also known as CCL4, is a chemoattractant for natural killer cells, monocytes and a variety of other immune cells. MIP-1p is one of the major HIV suppressive factors produced by CD8+ T cells. MIP-1β has been additionally implicated in diabetes, arthritis, and arthrosclerosis. Increased expression of MIP-1β has been found in the brain of patients with epilepsy.

P-Cadherin is a classical cellular adhesion molecule, localized to isolated tissues. The designation "P" indicates its expression in the placenta, but P-cadherin is additionally found in tissues such as hair follicles, keratinocytes, mammary myoepithelium, melanocytes, prostate, retina, serum, and skin. Due to a relative lack of characterization compared to other cadherins, expression and functional data are limited. P-Cadherin has been implicated in breast cancer and other malignancies. P-Cadherin has yet to be linked to epilepsy.

Osteoactivin, also known as glycoprotein nonmetastatic melanoma protein B (GPNMB), is a transmembrane glycoprotein involved in regulation of the extracellular matrix of several cell types. Functions include regulation of cell proliferation, adhesion, differentiation, and synthesis of extracellular matrix proteins. Osteoactivin is crucial for the differentiation and function of osteoclasts and osteoblasts. Altered expression of osteoactivin has been reported in osteoarthritis, breast cancer, melanoma, and glioblastoma. Neuroprotective effects of osteoactivin have been noted in ALS and ischemic injury. Osteoactivin has not been directly linked to epilepsy.

Macrophage colony-stimulating factor (M-CSF), also known as colony stimulating factor (CSF)-1, is a cytokine that stimulates macrophage proliferation, differentiation, and survival. Increased serum M-CSF have been noted during pregnancy and immune thrombocytopenic purpura. Abnormal levels of M-CSF have also been associated with neurological diseases, brain tumors, and other malignancies. M-CSF has not been linked to epilepsy.

IL-7 is a cytokine secreted mainly by stromal cells, but can also be produced by keratinocytes, dendritic cells, hepatocytes, neurons, and epithelial cells. Its main function is for the differentiation, growth, and survival of lymphocytes. IL-7 plays a fundamental role in T-cell development, peripheral T-cell homeostasis, and immune tolerance. IL-7 has been implicated in autoimmune diseases, muscle hypertrophy, and cancer. Increased IL-7 expression has been found in brain tissue of patients with epilepsy.

MCP-2, also known as CCL8, is a chemokine that attracts monocytes, lymphocytes, basophils and eosinophils, recruiting T-cells to sites of inflammation. Increases in MCP-2 has been noted in tuberculosis, arthritis, multiple sclerosis, allograft rejection, and arthrosclerosis. MCP-2 has not previously been investigated in relationship to epilepsy.

The abbreviation "IP-10" refers to interferon gamma-induced protein 10, small-inducible cytokine B10, C-X-C motif chemokine 10 (CXCL10), or variants thereof. IP-10 is a chemoattractant for monocytes, T-cells, NK cells, and dendritic cells.

Eotaxin, also known as eotaxin-1, refers to chemokine (C-C motif) ligand 11 (CCL11), or variants thereof. Eotaxin is a potent chemoattractant for eosinophils.

Eotaxin-2 refers to chemokine (C-C motif) ligand 24 (CCL24), or variants thereof. Eotaxin-2 is chemoattractant for eosinophils.

Eotaxin-3 refers to chemokine (C-C motif) ligand 26 (CCL26), or variants thereof.

The abbreviation "VCAM-1" refers to vascular cell adhesion molecule 1 or cluster of differentiation 106 (CD106). VCAM-1 mediates cellular adhesion molecule of lymphocytes, monocytes, eosinophils, and basophils to the vascular endothelium. VCAM-1 may be detected in soluble form (sVCAM1).

The abbreviation "VEGF-A" refers to vascular endothelial growth factor A. VEGF-A is a growth factor for endothelial cells.

Interleukin 5 (IL5) is an interleukin produced by type-2 T helper cells and mast cells. MIP-5 refers to macrophage inflammatory protein 5, also known as CCL15 or hemofiltrate CC chemokine-2. MIP-5 is a chemokine primarily expressed in heart and skeletal muscle.

TNF-β refers to tumor necrosis factor β, also known as Lymphotoxin-alpha. TNF-β is a cytokine involved in proliferation, cell survival, differentiation, and apoptosis.

MIF refers to macrophage migration inhibitory factor, also known as glycosylation-inhibiting factor (GIF), L-dopachrome isomerase, or phenylpyruvate tautomerase. MIF is an important regulator of innate immunity.

Nectin-4 is a cellular adhesion molecule.

TNF-RI refers to tumor necrosis factor receptor 1, also known as tumor necrosis factor receptor superfamily member 1A (TNFRSF1A) or CD120a. TNF-RI is a ubiquitous receptor that binds TNF-α.

TNF-RII refers to tumor necrosis factor receptor 2, also known as tumor necrosis factor receptor superfamily member 1B (TNFRSF1B) or CD120b. TNF-RII is a membrane receptor that binds TNF-α.

IL-8 refers to interleukin 8, also known as chemokine (C-X-C motif) ligand 8 (CXCL8). IL-8 is a chemokine produced by macrophages and other cell types.

MCP-1 refers to monocyte chemoattractant protein-1, also known as chemokine C-C motif) ligand 2 (CCL2) and small inducible ligand A2. MCP-1 recruits monocytes, memory T-cells, and dendritic cells to sites of inflammation.

CRP refers to C-reactive protein, an acute phase inflammatory protein produced by the liver.

Calbindin refers to calcium binding proteins.

MMP-1 refers to matrix metalloproteinase-1, also known as interstitial collagenase and fibroblast collagenase. MMP-1 is involved in the breakdown of the extracellular matrix.

MMP-9 refers to matrix metalloproteinase-9, also known as 92 kDa type IV collagenase, 92 kDa gelatinase, or gelatinase B. MMP-9 is involved in the breakdown of the extracellular matrix.

Osteonectin refers to a glycoprotein in the bone that binds calcium, also known as secreted protein acidic and rich in cysteine (SPARC) or basement-membrane protein 40.

IL-12/IL-23p40 refers to the p40 subunit of interleukin-12 and interleukin-23, which are heterodimers that share the p40 subunit.

IL-1a refers to interleukin-1alpha, also known as hematopoietin 1. IL-1a is a cytokine that produces inflammation and promotes fever and sepsis.

SCF refers to stem cell factor, also known as KIT-ligand or steel factor. SCF is a cytokine that binds to the c-KIT receptor.

Cytokeratin-8 refers to keratin type II cytoskeletal 8, also known as keratin-8.

IL-17A refers to interleukin-17A, a pro-inflammatory cytokine produced by activated T-cells.

IL-15 refers to interleukin-15, a cytokine that induced proliferation of natural killer cells.

MDC refers to macrophage derived chemokine, also known as chemokine (C-C motif) ligand 22 (CCL22). MDC is a chemokine secreted by dendritic cells and macrophages.

IL-10 refers to interleukin 10, also known as human cytokine synthesis inhibitory factor (CSIF). IL-10 is an anti-inflammatory cytokine produced by monocytes and lymphocytes.

MIP-1alpha or MIP-1a refers to macrophage inflammatory protein-1, also known as chemokine (C-C motif) ligand 3. MIP-1a is involved in acute inflammatory response, recruiting leukocytes.

GM-CSF refers to granulocyte macrophage colony stimulating factor, also known as colony stimulating factor 2 (CSF2). GM-CSF is a monomeric glycoprotein that functions as a cytokine.

IFN-γ refers to interferon-gamma, a cytokine that is critical for innate and adaptive immunity.

IL-13 refers to interleukin-13, a mediator of allergic inflammation.

IL-1B refers to interleukin-1beta or IL-1β, also known as leukocytic pyrogen, leukocytic endogenous mediator, mononuclear cell factor, and lymphocyte activating factor. IL-1B is an important cytokine mediating inflammatory responses.

IL-12p70 refers to the heterodimer of interleukin-12, also known as IL-12, cytotoxic lymphocyte maturation factor, natural kill stimulatory factor. IL-12p70 is a cytokine composed of protein products from two separate genes, IL12A and IL12B. IL-12 is involved in the differentiation of T-cells into Th1 cells.

IL-2 refers to interleukin-2, a cytokine that regulates the activities of leukocytes.

IL-4 refers to interleukin-4, a cytokine that induces differentiation of Th0 cells to Th2 cells.

IL-6 refers to interleukin-6, a cytokine with both pro-inflammatory and anti-inflammatory functions.

As indicated in the description of some of the proteins, some markers had not previously been investigated in regards to epilepsy, and others may have been investigated in animal models or in dissected or post-mortem brain tissue. This work provides therefore several novel biomarkers that can be detected in patient plasma that relates to a patient with epilepsy. In addition, the combination of biomarkers provides a novel mechanism for identifying patients with epilepsy.

As shown herein, the described invention ameliorates the deficiencies in the field. Indeed, based on a link between inflammation and seizures both in experimental models and in humans with epilepsy, an initial proteomics screen in patient plasma was used to probe a panel of biomarkers linked to inflammatory cytokines, chemokines, enzymes, and cellular adhesion molecules that were hypothesized to exhibit phasic or tonic changes in response to seizures in our studies. It was speculated that measurable changes in levels of specific plasma proteins could yield a diagnostic blood test for seizures.

In epilepsy an immune response is generated within the region of seizure onset. In several distinct tissue lesion types such as tuberous sclerosis (TSC) and mesial temporal sclerosis (MTS), pro-inflammatory cytokines such as IL-1β, IL-6, TNF-α, Fas, and Fas-ligand are activated. In addition, there is complement fixation and deposition, altered blood-brain barrier permeability, and macrophage infiltration. Inflammation may generate a wide variety of downstream effects including upregulation of IL-16 production, activation of TLR4, NFκB, mTOR, and MAPK cascades, attraction of activated lymphocytes, microglia, and macrophages, and alteration of astrocyte physiology. Additionally, the relative balance with anti-inflammatory cytokines can also be modulated, demonstrating a change in levels of cytokines like IL-4, IL-10 and IL-13. Without being bound by theory, these changes may be a result of a disease process leading to seizures, caused by seizures, and/or be the result of seizures (see FIG. 1). Diagnostic tests and algorithms developed are able to distinguish seizures from a lack of seizure, and epilepsy from normal (see FIG. 2) The present application addresses a need in the art for markers associated with seizures.

Definitions

The terms "comprising" and "including" are used interchangeably, unless otherwise noted.

The term "cryptogenic" is used herein to refer to a seizure or epilepsy of unknown origin.

The term "phasic" is used herein to refer to a change in blood biomarkers directly related to an immediate or sudden event or seizure. The change in the blood is short-lived and resolves within a specific period of time after the event.

The term "tonic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The term "acute" is used herein to refer to a change in blood biomarkers directly related to an immediate or sudden event or seizure. The change in the blood is short-lived and resolves within a specific period of time after the event.

The term "chronic" is used herein to refer to persistent or constantly changes in blood biomarkers related to a patient's over-arching condition. The levels are distinguishable from those in control subjects and do not fluctuate markedly based on whether the patient has experienced an event symptomatic of his or her condition.

The terms "disease", "disorder", or "condition" are used herein to refer to any manifestations, symptoms, or combination of manifestations or symptoms, recognized or diagnosed as leading to, causing, or influencing seizure. The terms include, but are not limited to, traumas, inflammatory and autoimmune responses, physiological malformations, and genetic defects.

The term "ictal" refers to a physiologic state or event such as a seizure.

The term "indicative" (or "indicative of") encompasses both prediction/forecasting (including tendency), and detection (proximate to the occurrence of a seizure), and unless otherwise noted, embodiments encompassing the term are intended to define and encompass embodiments specific to prediction, specific to detection, and for prediction as well as for detection of a past or current event. Use of the term indicative in conjunction with the term "tendency" is intended solely for emphasis of evidence of a past event versus a tendency, predicting or forecasting toward a future event, but the use solely of indicative is intended to encompass tendency unless otherwise indicated.

The term "sample" is used herein to refer to a blood plasma or blood serum sample, unless otherwise noted. In each embodiment described herein, the use of blood plasma is contemplated as an independent embodiment from the alternative of blood plasma or blood serum. In each embodiment described herein, the use of blood serum is contemplated as an independent embodiment from the alternative of blood plasma or blood serum. In each embodiment described herein, the use of another biological sample, including but not limited to cerebrospinal fluid (CSF), a tissue sample obtained by resection, saliva, and urine is contemplated according to conventional techniques in the art for obtaining the sample and for analysis of same. The sample can be treated prior to use, such as preparing plasma from blood, diluting viscous fluids, and the like. Methods of treatment can involve filtration, distillation, extraction, concentration, inactivation of interfering components, the addition of reagents, and the like.

The terms "seizure" and "epilepsy" are used interchangeably, two unprovoked seizures being required for a clinical diagnosis of epilepsy, unless otherwise noted. The term epilepsy may also be defined by the understanding of, or theories of, seizure as understood as of the time of filing of the application. Epilepsy includes and is not limited to all forms of epilepsy.

The terms "subject", "individual", and "patient" are used interchangeably herein to refer to a mammal from which a sample is taken, unless otherwise noted. The terms are intended to encompass embodiments specific to humans. A subject, individual or patient may be afflicted with, at risk for, or suspected of having a tendency to have seizure or a disorder for which seizure is symptomatic. The term also includes domestic animals bred for food or as pets, including horses, cows, sheep, pigs, cats, dogs, and zoo animals. Typical subjects for treatment include persons susceptible to, suffering from or that have suffered one or more seizures. In particular, suitable subjects for treatment in accordance with the invention are persons that are susceptible to or that have suffered one or more seizures.

The term "tendency", e.g., "tendency to have seizure", is intended to refer to a reasonable medical probability of an event, e.g., seizure to occur or recur. The term also encompasses the frequency with which such events may occur before, after, or during ongoing treatment.

As used herein, the term "treat" or "treating" refers to any method used to partially or completely alleviate, ameliorate, relieve, inhibit, prevent, delay onset of, reduce severity of and/or reduce incidence of one or more symptoms or features of a particular condition, in any clinical setting e.g., seizure or a seizure-related disorder. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, frequency thereof, or of one or more symptoms associated with such condition. The terms "treatment" and "therapeutically" refer to the act of treating, as "treating" is defined above. The purpose of intervention is to combat the condition and includes the administration of therapy to prevent or delay the onset of the symptoms or complications, or alleviate the symptoms or complications, or eliminate the condition. For example, a treatment may be used to ameliorate symptoms or frequency thereof (e.g., frequency of seizure) associated with a disorder. Treatment can be a therapeutic, an external device or internal or implantable device that helps to control and minimize seizures and epilepsy.

The terms "tuberous sclerosis", "tuberous sclerosis complex", and the abbreviation/acronyms "TS" and "TSC", are used interchangeably herein.

IL-16

IL-16 is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding IL-16 in blood plasma or blood serum of a mammalian subject, wherein an altered plasma or serum concentration of IL-16 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

MMP-3

MMP-3 is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding MMP-3 in blood plasma or blood serum of a mammalian subject, wherein an altered plasma or serum concentration of MMP-3 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TRAIL

TRAIL is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding TRAIL in blood plasma or blood serum of a mammalian subject, wherein an altered plasma or serum concentration of TRAIL relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

P-Cadherin

P-Cadherin is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding P-cadherin in blood plasma or blood serum of a mammalian subject, wherein an altered plasma or serum concentration of P-cadherin relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TARC

TARC is also an effective marker, differentially distributed in the blood plasma or blood serum of epilepsy patients relative to healthy patients and it is shown to be elevated in seizure patients.

In another embodiment, a polypeptide expression panel or array is provided, the panel or array comprising a probe capable of binding TARC in blood plasma or blood serum of a mammalian subject, wherein an altered plasma or serum concentration of TARC relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

TNF-$\alpha$

TNF-$\alpha$ is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding TNF-$\alpha$ in blood plasma or blood serum of a mammalian subject, wherein an altered plasma or serum concentration of TNF-$\alpha$ relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

MIP-1$\beta$

MIP-1$\beta$ is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding MIP-1$\beta$ in blood plasma or blood serum of a mammalian subject, wherein an altered plasma or serum concentration of T MIP-1$\beta$ relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

MCP-1 or CCL2

MCP-1 is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding MCP-1 in blood plasma or blood serum of a mammalian subject, wherein an altered plasma or serum concentration of T MCP-1 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

VCAM-1 or sVCAM1

VCAM-1 is also an effective marker, differentially distributed in the blood plasma or blood serum of epilepsy patients relative to healthy patients and it is shown to be reduced in seizure patients.

In another embodiment, a polypeptide expression panel or array is provided, the panel or array comprising a probe capable of binding VCAM-1 in blood plasma or blood serum of a mammalian subject, wherein an altered plasma or serum concentration of VCAM-1 relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Other Markers Contained Herein

Other markers contained herein can also an effective marker(s), differentially distributed in the blood plasma or blood serum of epilepsy patients relative to healthy patients and it is shown to be reduced in seizure patients.

In another embodiment, a polypeptide expression panel or array is provided, the panel or array comprising a probe capable of other markers contained herein in blood plasma or blood serum of a mammalian subject, wherein an altered plasma or serum concentration of other markers contained herein relative to a healthy control is indicative of seizure or a tendency to have seizure.

Individual measurements may be taken and analyzed individually or in any combination using linear or logarithmic units, or by using ratios of linear or logarithmic units. The reciprocals of ratios of linear or logarithmic units may also be used.

Biomarker Ratios

In further embodiments, a polypeptide or array comprising a probe capable of binding one, two or more biomarkers in blood plasma or blood serum of a mammalian subject, wherein a change in plasma or serum concentration ratio in tested subjects relative to control (healthy, non-epileptic/non-seizure) is altered relative to healthy controls and is indicative of a seizure or a tendency to have seizure. In some embodiments, the biomarkers can be any combination of those biomarkers described herein, including but not limited to TARC, TNF-α, IL-16, MMP-3, TRAIL, and P-cadherin.

Individual measurements may be taken and analyzed individually or in any combination using linear or logarithmic units, or by using ratios of linear or logarithmic units. The reciprocals of ratios of linear or logarithmic units may also be used.

Combination of Individual Measures and Ratios

In further embodiments, a polypeptide or array comprising a probe capable of binding one, two or more biomarkers in blood plasma or blood serum wherein a change in plasma or serum concentration of two or more biomarkers and the change of the ratio of two or more biomarkers in tested subjects relative to control (healthy, non-epileptic/non-seizure) is altered relative to healthy controls and is indicative of a seizure or a tendency to have seizure. Any combinations of individual concentrations and ratios may be used.

Individual measurements may be taken and analyzed individually or in any combination using linear or logarithmic units, or by using ratios of linear or logarithmic units. The reciprocals of ratios of linear or logarithmic units may also be used.

Patient Demographic Characteristics

In another embodiment, when combined any biomarkers concentrations for one or more biomarkers measured in blood plasma or serum, combined with patient demographics or other characteristics associated with the patient, including but not limited to age, sex and/or race may indicate a seizure having occurred or a tendency to have a seizure in comparison to relative normal or healthy controls.

When combined with patient demographic characteristics, the individual measurements may be taken and analyzed individually or in any combination using linear or logarithmic units, or by using ratios of linear or logarithmic units. The reciprocals of ratios of linear or logarithmic units may also be used.

Other BioMarkers

Additional markers that are useful include, alone or in combination, include IL-1B, IL-2, IL-6, IL-8, IL-10, IL-12p70, IFN-γ, IL-13, IL-4, TNF-α, IL-17A, GM-CSF, IL-12/IL-23p40, IL-15, IL-16, IL-1 a, IL-5, IL-7, TNF-β, VEGF-A, MCP-1/CCL2, Eotaxin, Eotaxin-3, IP-10, MCP-4, MDC, MIP-1 a, MIP-1β, TARC, sICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL. Still additional markers that are useful include, alone or in combination, IL-1alpha, IL-3, IL-9, IL-22, IFN-alpha, CCL11, CX3CL1, HMGB1, bFGF, PDGFbeta, Fas, Fas-ligand, BDNF, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

The panels or arrays of the invention may also include one or more probes capable of binding one or more of the biomarkers listed herein, wherein an altered plasma or serum concentration of one or more relative to a healthy control is indicative of seizure or a tendency to have seizure. Still additional markers that are useful include, alone or in combination, IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In another embodiment, a method for predicting or detecting a seizure is provided, comprising contacting a blood plasma or blood serum sample obtained from a mammalian subject with a diagnostic reagent that can measure or detect the expression level of one or more biomarkers, wherein a change in plasma or serum concentration of one or more biomarkers relative to a healthy control indicates a seizure having occurred or a tendency to have seizure. Individual measurements may be taken and analyzed individually or in any combination using linear or logarithmic units, or by using ratios of linear or logarithmic units. The reciprocals of ratios of linear or logarithmic units may also be used.

In another embodiment, a method for predicting or detecting epilepsy is provided, comprising contacting a blood plasma or blood serum sample obtained from a mammalian subject with a diagnostic reagent that can measure or detect the expression level of one or more biomarkers, wherein a change in plasma or serum concentration of one or more biomarkers relative to a healthy control indicates epilepsy. Individual measurements may be taken and analyzed individually or in any combination using linear or logarithmic units, or by using ratios of linear or logarithmic units. The reciprocals of ratios of linear or logarithmic units may also be used. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet another embodiment, a method for assessing the effectiveness of a treatment of seizure or a disorder for which said seizure is symptomatic, the method including contacting a first blood plasma or blood serum sample obtained from a mammalian subject prior to treatment with one or more diagnostic reagents that can measure or detect the expression level of one or more biomarkers and contacting a second blood plasma or blood serum sample obtained from a mammalian subject subsequent to treatment with a diagnostic reagent that can measure or detect the expression level of one or more biomarkers, wherein an altered plasma or serum concentration of one or more biomarkers relative to the first blood plasma or blood serum sample indicates effectiveness in treatment of seizure or a disorder for which seizure is symptomatic. The method may further include contacting the first blood plasma or blood serum sample and the second blood plasma or blood serum sample with one or more diagnostic reagents that can measure or detect the expression of Fas, Fas-ligand, IL-1alpha, IL-3, IL-9, IL-22, IFN-alpha, CCL11, CX3CL1, HMGB1, bFGF, PDGFbeta, Eotaxin-3, Eotaxin, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In still further embodiments, a method for determining whether or not one or more seizures are resultant from inflammation, comprising contacting a blood plasma or blood serum sample obtained from a mammalian subject with a diagnostic reagent that can measure or detect the expression level of one or more biomarkers and/or contacting a blood plasma or blood serum sample obtained from a mammalian subject with a diagnostic reagent that can measure or detect the expression level of one or more biomarkers, wherein an altered plasma or serum concentration of one or more biomarkers relative to a healthy control indicates an inflammatory basis or component of seizure. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

In yet other embodiments, a method for determining whether or not seizure is likely to occur in a subject is provided, comprising contacting a blood plasma or blood serum sample obtained from a mammalian subject with a diagnostic reagent that can measure or detect the expression level of one or more biomarkers and/or contacting a blood plasma or blood serum sample obtained from a mammalian subject with a diagnostic reagent that can measure or detect the expression level of one or more biomarkers, wherein an altered plasma or serum concentration of one or more biomarkers relative to a healthy control indicates a tendency to have seizure. The method may further include contacting the first blood plasma or blood serum sample and the second blood plasma or blood serum sample with one or more diagnostic reagents that can measure or detect the expression of IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin E2, nerve growth factor (NGF), CCL-5 (RANTES). Probes may further include, alone or in combination, α1AT, and HGF. Probes may also include one or more components of the complement cascade, e.g., C1q, C3c and C3d. Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-6 family members (TGF-β1 to -β5). Individual measurements may be taken and analyzed individually or in any combination using linear or logarithmic units, or by using ratios of linear or logarithmic units. The reciprocals of ratios of linear or logarithmic units may also be used.

For any biomarker selected, individual measurements may be taken and analyzed individually or in any combination using linear or logarithmic units, or by using ratios of linear or logarithmic units. The reciprocals of ratios of linear or logarithmic units may also be used.

In further embodiments of the above, the seizure may be associated with temporal lobe epilepsy. In a further embodiment, the temporal lobe epilepsy may be mesial temporal sclerosis (MTS). In other embodiments, the seizure may be associated with tuberous sclerosis complex (TSC).

In further embodiments, the seizure may be classified according to the: Operational Classification of Seizure Types by the International League Against Epilepsy, which is located at the following web address: www.ilae.org/visitors/centre/documents/ClassificationSeizureILAE-2016.pdf.

In still other specific further embodiments of the above, the seizure may be cryptogenic. In further embodiments, the seizure is not associated with immune response to a pathogen.

The embodiments, including the probes and panels/arrays of probes, described herein may be used to detect whether or not a seizure has (or is likely to have) occurred. They may also be used to predict the likelihood of further seizure. Additionally, they may be used to predict whether or not seizure is likely following a brain injury or head trauma. They are also useful in identifying whether or not a seizure is the result of an inflammatory process. Further, they may be used in assessing whether or not a treatment is effective.

By way of non-limiting example, the following polypeptide panels or arrays are embodiments of the application (the terms altered, elevated, and altered refer to the expression level in the epileptic patient versus that in a healthy subject):
TARC;
TNF-α;
IL-16;
MMP-3;
TRAIL;
P-Cadherin
MIP-1β
MCP-1
VCAM-1
Plus any combination of one or more of TARC, TNF-α, IL-16, MMP-3, TRAIL, P-Cadherin, MIP-1β, MCP-1 and VCAM-1

Other polypeptide panels or arrays are embodiments of the application, and may include the above and additionally one or more of the following:
IL-1B, IL-2, IL-6, IL-8, IL-10, IL-12p70, IFN-γ, IL-13, IL-4, IL-17A, GM-CSF, IL-12/IL-23p40, IL-15, IL-16, IL-1α, IL-5, IL-7, TNF-β, VEGF-A, MCP-1/CCL2, Eotaxin, Eotaxin-3, IP-10, MCP-4, MDC, MIP-1α, MIP-1β, sICAM1, sVCAM1, CRP, SAA, MMP-9, Calbindin, Eotaxin-2, MIP-5, MMP-1, Osteoactivin, TNF-RI, TNF-RII, MIF, Cytokeratin-8, MCP-2, M-CSF, Nectin-4, Osteonectin, SCF
IL-1alpha, IL-3, IL-9, IL-22, IFN-alpha, CCL11, CX3CL1, HMGB1, bFGF, PDGFbeta, Fas, Fas-ligand, BDNF, Eotaxin-3, Eotaxin, substance P and prostaglandin E2, nerve growth factor (NGF), CCL-5 (RANTES), α1AT, and HGF
one or more components of the complement cascade, e.g., C1q, C3c and C3d.
Still additional markers that may be useful in the invention, and that may provide information on anti-inflammatory response, include, alone or in combination, IL-1 receptor antagonist, IL-4, IL-11, IL-13, leukemia inhibitory factor, interferon-alpha, and TGF-β family members (TGF-β1 to -β5).

Samples may be obtained from patients by conventional techniques. These techniques may include those covered by an institutional review board (IRB) approved protocol, including blood, urine, saliva and CSF. In one embodiment, the samples are anticoagulated using sodium citrate. In a further embodiment, plasma is prepared by centrifuging samples, e.g., at 5,000 g (g=gravity) for 15 minutes at 4° C. Control samples may also be purchased from commercial vendors.

Levels (concentrations) of the polypeptide to be quantified in plasma may be obtained by any of a number of methods known in the art, the particular procedure not being a limitation of the embodiments herein. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art. A variety of capture and detect antibodies may be used to detect biomarkers by those skilled in the art. Single- and multi-probe kits are available from commercial suppliers, e.g., Meso Scale Discovery. These kits include the kits referenced in the Examples hereto. Individual measurements may be taken and analyzed individually or in any combination using linear or logarithmic units, or by using ratios of linear or logarithmic units. The reciprocals of ratios of linear or logarithmic units may also be used.

Also described herein are methods of treating or preventing seizure or a disorder for which seizure is symptomatic in a mammalian subject or patient, comprising delivery of anti-inflammatories or other therapeutic agents targeting one or more of the biomarkers included herein. In a further embodiment, the mammal is a human. Treating patients with seizures and epilepsy with anti-inflammatory or other therapeutic agents targeting one or more of the biomarkers included herein in order to reduce seizures or epilepsy symptoms.

Anti-inflammatory or other therapeutic agent treatment or prevention targeting one or more of the biomarkers included herein may be made intravenous or via intra-cerebrospinal fluid (intra-CSF) by techniques known to one of skill in the art. Delivery of anti-inflammatory or other therapeutic agent treatment or prevention targeting one or more biomarkers included herein may also be made by any other suitable means, including but not limited to orally, orally with suitable carrier or excipient, extended or controlled release dosing, skin patches or other external extended release mechanism, absorption through the skin, drug delivery mechanisms, intravenously, targeted delivery systems, delivery systems designed to cross the blood brain barrier, intravenously via pump or similar mechanism for on-demand or automated delivery, inhaled, injected, emergency injections (such as epi-pens) and intranasal delivery to the CSF with a suitable carrier or excipient.

Anti-inflammatory other therapeutic agent treatment targeting one or more of the biomarkers included herein may be administered by a device that determines the levels of concentration of the biomarkers defined herein, makes an assessment of the markers relative to normal controls or previously measured levels of a patient, and makes determinations to either increase, decrease or remain the same with respect to current therapeutic dosage and or protocols.

Other Applications

In some embodiments of the invention, biomarkers and algorithms that form a blood-based diagnostic test, such as EvoScore, as described herein, can be leveraged for seizure prediction; anti-epileptic drug (AED) clinical trial eligibility, endpoints, and effectiveness; multiple diagnostic combinations including EEG, MRI, Genomics, Genetics and proteomics, companion diagnostics; and potential identification of inflammation based therapeutics and response. In some embodiments, the blood-based diagnostic test described herein may be used to determine absolute changes in biomarker levels in an event as well as relative changes in biomarkers in a patient over time. In some embodiments, the biomarkers and algorithms in the blood-based diagnostic test described herein in known epilepsy patients who are well-controlled with medications, may be used to prepare a corresponding score and a user may determine if the score correlates with AED responsiveness and, by extension, predict subsequent breakthrough seizures and medical intractability. Similarly, the blood-based diagnostic test described herein may be used to predict AED response in newly identified epilepsy patients to quickly assess therapeutic response. In medically refractory patients after epilepsy surgery, the blood-based diagnostic test described herein may, in some embodiments, be provided that is predictive of surgical success. In some embodiments, the blood-based diagnostic test described herein, can be used to assess patients at risk for seizures following, for example, head injury or stroke to determine if their risk of seizures is increased. Furthermore, there is an important potential use in AED clinical trials to ensure more robust enrollment criteria resulting in faster, smaller trials allowing new medicines to reach patients earlier. In some embodiments, the blood-based diagnostic test described herein can be used as a personalized medicine diagnostic, to allow treatment and tracking of seizures and epilepsy over time, at defined intervals, to establish individualized response to therapies, effectiveness, control, and prediction of future events in order to improve patient quality of life and reduce burden on the healthcare system. In certain embodiments, the foregoing blood-based diagnostic test of the invention is EvoScore.

Test Methods

Blood was collected from human neurology patients or normal controls into lavender-topped vacutainer blood collection tubes containing $K_2$EDTA as an anticoagulant (BD Biosciences). The blood collection tubes were inverted eight times, and then placed on wet ice at 4° C. for 10-15 minutes before centrifuging. The blood was centrifuged at 1000 RCF for 10 minutes at 4° C. Plasma supernatant was aliquotted into sterile 2 ml microtubes (Sarstedt, Type I) and frozen at −70° C. to −80° C.

Protein levels in human plasma were measured by sandwich ELISA with electrochemiluminescent detection using multiplexed assay plates from Meso Scale Discovery (MSD) (Gaithersburg, MD) and analyzed on the MSD Sector Imager 2400. The following assay plates were used: Proinflammatory Panel 1, Cytokine Panel 1, Chemokine Panel 1, Vascular Injury Panel 2, Screen Panel A, and Screen Panel B. Together, the panels assessed the levels of the following proteins: IL-1B, IL-2, IL-6, IL-8, IL-10, IL-12p70, IFN-γ, IL-13, IL-4, TNF-α, IL-17A, GM-CSF, IL-12/IL-23p40, IL-15, IL-16, IL-1α, IL-5, IL-7, TNF-β, VEGF-A, MCP-1/CCL2, Eotaxin, Eotaxin-3, IP-10, MCP-4, MDC, MIP-1α, MIP-1β, TARC, sICAM1, sVCAM1, CRP, SAA, MMP-9, MMP-3, Calbindin, Eotaxin-2, MIP-5, MMP-1, Osteoactivin, P-cadherin, TNF-RI, TNF-RII, MIF, Cytokeratin-8, MCP-2, M-CSF, Nectin-4, Osteonectin, SCF, and TRAIL.

Each plate was coated with specific capture antibodies with up to 10 distinct spots per well in a 96-well format. MSD provided the antibodies and coated the plates, accordingly.

For all incubation steps, plates were sealed with adhesive plate seals and incubations were performed at room temperature (RT) with rotation (705 pm) on a microtiter plate shaker (Denville 210A #C0210). In all wash steps, wells were emptied and then washed three times with 300 μL of Phosphate Buffered Saline (PBS) with 0.05% Tween-20 (Wash Buffer, MSD). Reverse pipetting was employed to avoid the production of bubbles throughout the assay.

To run samples, coated plates were removed from 4° C. and allowed to equilibrate to room temperature for 30 to 60 minutes, after which each plate was washed three times with wash buffer prior to adding protein standard and sample for the assay.

Protein standards for each of the markers were provided by MSD and prepared per MSD assay guidelines. Protein standards and human plasma samples were diluted in the same diluent, but varied per assay panel. The following dilution of sample and diluent was used for each assay panel: 2-fold dilution in diluent 2 for Proinflammatory Panel 1, 2-fold dilution in diluent 43 for Cytokine Panel 1, 4-fold dilution in diluent 43 for Chemokine Panel 1, 1000-fold dilution in diluent 101 for Vascular Injury Panel 2, 10-fold dilution and diluent 7 for Screen Panel A, and 2-fold dilution and diluent 2 for Screen Panel B. Fifty μL of protein standard or diluted sample was plated in duplicate on each plate, according to MSD assay guidelines. Standards and samples were incubated for two hours at room temperature.

After incubation, plates were washed three times with wash buffer. SULFO-TAG labeled detection antibodies for each target protein were provided by MSD. Antibodies were combined as per MSD assay protocol in diluent 3 for all assay panels except the Vascular Injury Panel 2, where diluent 101 was used. 100 μl of diluted detection antibodies were added to each well in a multiplexed fashion (separately for each target assay plate). Antibodies were incubated for two hours at room temperature.

Plates were then washed with wash buffer prior to developing and reading the assay.

4×MSD Read Buffer T was diluted to 2× with sterilized reverse-osmosis $H_2O$. Plates were developed by adding 150 μL of RT 2× Read Buffer T to each well, and then read immediately on the MSD Sector Imager 2400 coupled with the MSD Discovery Workbench 4.0 software. MSD Discovery Workbench 4.0 software was used to determine the protein concentrations of the plasma samples, final concentrations of protein values were determined by multiplying by the dilution factor for each assay.

Patient Enrollment

A clinical trial was performed to determine whether EvoScore can be used effectively and accurately to diagnose patients with seizures, and to establish the threshold for diagnosis. All inpatient and outpatient subjects were 18 years of age or older and cognitively able to give informed consent. Subjects aged 18-20 provided assent, and a legally authorized representative gave consent on their behalf. There were no ethnic or gender limitations for these studies, and all eligible patients were recruited to ensure that there was no selection bias.

Inpatients admitted to an epilepsy monitoring unit (EMU) were invited to give a single sample of 15 ml of blood each morning and an additional 15 ml sample of blood following a seizure or seizure-like event. Inpatient subjects' EvoScore results were compared with all of their individual event diagnoses during their EMU stay, and their ultimate patient diagnosis at the conclusion of their EMU stay.

Outpatients were eligible to join the study only if they were attending their first visit at the outpatient neurology clinic for evaluation of their suspected seizures; these patients did not yet have a diagnosis of their events as either epileptic or non-epileptic. Outpatient subjects gave a single 15 mL sample of blood for research, and the study team collected all available clinical information relevant to their diagnostic workup for approximately 6 months after they joined the study. After six months, a team of independent neurologists evaluated their relevant medical history and "diagnosed" the subjects, and this diagnosis was compared to the EvoScore results to determine diagnostic accuracy (agreement among two epileptologists was sufficient).

Subjects 21 years of age and older who accompanied patients to epilepsy center appointments were considered to be normal controls and were eligible to join the study if they were cognitively able to provide informed consent, had not been diagnosed with epilepsy, and were not taking any anti-epileptic drugs for any reason. A total of 401 study subjects were enrolled overall. 240 outpatients, 131 inpatients, and an additional 30 controls were enrolled from both the inpatient EMU and the outpatient neurology clinic. For the inpatient and outpatient subjects, the average age was 36.5 (range 18-82) and 52% were female (n=209).

Explanation of Individual Event Diagnosis (IED) and Patient Diagnosis (PD)

Inpatients initiated and ended their stays in the EMU. Outpatients were recruited from a neurology outpatient clinic, but some returned for a stay in the EMU. For all patients that stayed in the EMU, EMU reports were examined and the time was recorded of any observed neurological event immediately prior to the blood draw. The description of the event was also recorded, and neurologists independently diagnosed each individual event (Individual Event Diagnosis). Events were characterized as Non-Epileptic events (IED0), Epileptic events (with a positive EEG) (IED1), Unclear diagnosis event (IED2), or no event recorded (when there was no record of any event in the EMU report during that EMU stay) (IED3). When there was not agreement on the event diagnosis, the EMU reports were consulted and a consensus was reached. If no consensus could be reached, the event was rated with an unclear diagnosis (IED2). Individual event diagnosis is considered evaluation of phasic changes. Individual event diagnosis can also be called event diagnosis.

The final overall patient diagnosis recorded in the "Epilepsy Diagnosis" section of the EMU report was used for each patient for the Patient Diagnosis (PD). Patients either received a diagnosis of Non-Epilepsy (PD0), Epilepsy (PD1), Epilepsy+Other Non-Epileptic condition PD2), or an Unclear diagnosis (PD3). Patient diagnosis is considered evaluation of tonic changes.

Predictive Models and Score

As used herein, a "predictive model," which term may be used synonymously herein with "multivariate model" or simply a "model," is a mathematical construct developed using a statistical algorithm or algorithms for classifying sets of data. Predictive models can provide an interpretation function; e.g., a predictive model can be created by utilizing one or more statistical algorithms or methods to transform a dataset of observed data into a meaningful determination of disease activity or the disease state of a subject. Algorithms developed herein, based upon concentrations and ratios of biomarkers, and or combined with patient demographic characteristics, identify the phasic and tonic changes (acute and chronic) associated with a seizure event. Individual measurements may be taken and analyzed individually or in any combination using linear or logarithmic units, or by using ratios of linear or logarithmic units. The reciprocals of ratios of linear or logarithmic units may also be used.

The predictive model can be used in all clinical settings for one or more of following purposes (a) ruling in or ruling out seizure; (c) assessing the patient quality of life by predicting when and if seizures will continue to occur; and (c) the ability of a therapeutic or therapeutic protocol to control the seizures over time.

As used herein, a "score" is a value or set of values selected so as to provide a quantitative measure of a variable or characteristic of a subject's condition, and/or discriminate, differentiate or otherwise characterize a subject's condition. The values(s) comprising the score can be based on, for example, a measured amount of one or more sample constituents obtained from the subject or from clinical parameters or from clinical assessments or any combination thereof. In certain embodiments the score can be derived from a single constituent parameter or assessment, while in other embodiments the score is derived from multiple constituents, parameters and/or assessments. The score can be based upon or derived from an interpretation function, e.g., an interpretation function derived from a particular predictive model using any of carious statistical algorithms known in the art. A "change in score" can refer to the absolute change in score, e.g., from one time point to the next, or the percent change in score, or the change in the score per unit of time. For example, a score referred to herein may be provided by a blood-based diagnostic test of the invention (e.g., EvoScore).

The score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative" or other form to convey results of phasic and/or tonic changes in the identification of seizure and epilepsy.

The predictive models and scores can be used in combination with any of the current standard diagnostic techniques, including EEG and MRI to develop an ultimate patient diagnosis. The predictive score would add improved accuracy in terms of sensitivity, specificity, positive predictive value and negative predictive value when combined with other standard diagnostic techniques.

Algorithm Objectives, Thresholds and Actionable Results

Scoring algorithms included in the blood-based diagnostic tests described herein (e.g., EvoScore) were developed by the following methodologies: (a) For individual event diagnosis of seizure or not: Classification Tree and Regression analysis and/or Multiple Logistic Regression which may include risk groups defined by the classification tree analysis; and (b) For patient diagnosis of epilepsy or not: Logistic regression and Multiple Logistic Regression including risk groups defined by classification tree analysis.

EvoScore algorithms and methodologies for both individual event diagnosis of seizure or not and patient diagnosis of epilepsy or not were determined to be a function of measurable changes of the concentration, natural logarithm scaled changes in the concentration, ratios of the biomarkers and ratios of the scaled concentrations of one or more biomarkers and can include patient physical characteristics, including age, sex and prescription information.

All of these methodologies and results yielded algorithms meeting diagnostic test clinical and market performance and accuracy objectives. The algorithms' predictive results are designed to maximize sensitivity and True Positives, and minimize False Negatives, and maximize accuracy and correctly classified. Specificity and True Negatives can also be maximized with minimal false positives.

Thresholds or quantitative boundaries can be set to both maximize individual diagnostic values and or optimize combinations of diagnostic values, including sensitivity, specificity, and positive and negative predicted value. Different embodiments of the algorithms can use different thresholds depending on the goals of the algorithm. Thresholds can ultimately determine how a score is interpreted as the individual test score can be used to rate and/or measure the phasic and tonic changes, rule in or rule out an event, evaluate patient quality of life and therapeutic effectiveness, by providing numerically "quantitative" or high, medium or low "qualitative" or Positive or Negative "qualitative." Ultimate selections of thresholds are driven by the maximization and/or optimization of one or more characteristics of diagnostic accuracy as desired for performance.

FIG. 1 defines diagnosis parameters between epileptic seizures, non-epileptic seizures, and no seizures.

FIG. 2 defines the objectives of the algorithm and ultimate actionable results.

The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy patients, drug controlled epilepsy patients and drug refractory patients. The test score and biomarkers can be analyzed and compared across patients, patient groups, other indications and normal controls, and across an individual patient over time for personalized medicine.

Combination Diagnostic and Therapeutic Approaches

To achieve the maximum therapeutic benefits for individual subjects, it is important to be able to specifically quantify and assess the subject's disease burden at any particular time, determine the effects of treatment on disease activity, and predict future outcomes. The embodiments of the present teachings identify multiple serum biomarkers for accurate clinical assessment of disease activity in subjects with acute and chronic disease.

Current therapeutic approaches for epilepsy, include and are not limited to therapeutically effective dose of an anti-epileptic compound selected from the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. New therapeutic approaches are currently in development and are applicable to diagnostic evaluation and can be combination diagnostic and therapeutic approaches.

In some embodiments, a blood-based diagnostic test of the invention (e.g., EvoScore) can evaluate known epilepsy patients who are well-controlled with medications to determine if the score correlates with AED responsiveness and by extension, if changes in EvoScore predict subsequent breakthrough seizures and medical intractability. In some embodiments, a blood-based diagnostic test of the invention (e.g., EvoScore) can predict AED response in newly identified epilepsy patients to quickly assess therapeutic response. In some embodiments, a blood-based diagnostic test of the invention (e.g., EvoScore) can be used to assess in medically refractory patients after epilepsy surgery to determine if the score can predict surgical success. In some embodiments, a blood-based diagnostic test of the invention (e.g., EvoScore) can be used to assess patients at risk for seizures following for example, head injury or stroke to determine if their risk of seizures is increased. In some embodiments, a blood-based diagnostic test of the invention (e.g., EvoScore) can be used as a personalized medicine diagnostic, to allow for the treatment and tracking of seizures and epilepsy over time, at defined intervals, to establish individualized response to therapies, effectiveness, control, and prediction of future events in order to improve patient quality of life and reduce burden on the healthcare system.

In some embodiments, a blood-based diagnostic test of the invention (e.g., EvoScore) can be used in combination with EEG, MRI and other diagnostic approaches described herein.

In other embodiments, EvoScore alone, or in combination with other biomarkers as described herein and/or other clinical tests, can be utilized in other neurological diseases/indications including migraine, Alzheimer's disease, Parkinson's disease, traumatic brain injury, stroke, infections and immune response to a pathogen, autoimmune response, immune response, tumors and other neurological diseases/indications with an inflammation component and/or effect.

Kits

In an embodiment, the invention provides a diagnostic kit comprising a polypeptide expression panel or array. The kit may also be predictive, useful in determining imminent risk of seizure or recurrence of seizure, or in assessing recurrence risk. The kit may also contain a syringe and/or vile for drawing blood. The kit may also contain a blood card or other repository to hold blood and lancet in order to draw blood for the patient to supply a drop or drops of blood on a card or other repository for analysis. The kit may contain one or more probes corresponding to the polypeptide markers of the panel or array. The kit may also contain an ELISA plate based on chemiluminescent, luminist or equivalent technology. A multiple and portable (M&P) ELISA may also be provided as part of a kit of an embodiment. Still other suitable components will be known to one of skill in the art, and are encompassed hereby. Kits may include software, computers and instruments for presenting the diagnostic result.

Other aspects of the present invention provide a kit for the kit comprising: (a) assay (b) instructions (c) computer or computer system to perform a method of the present invention, or, in (d) other embodiments, an algorithm that forms part of a method of the present invention.

Other embodiments comprise biomarker detection reagents packaged together in the form of a kit for conducting any of the assays of the present teachings. In certain embodiments, the kits comprise oligonucleotides that specifically identify one of more biomarker nucleic acids based on homology and/or complimentary with biomarker nucleic acids. The oligonucleotide sequences may correspond to fragments of the biomarker nucleic acids. For example, the oligonucleotides can be more than: 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody, control formulations (positive and/or negative), and/or a detectable label. Instructions for carrying out the assay, including optionally instructions for generating a score can be included in the kit. The assay can be in the form of ELISA as known in the art.

Additionally, biomarkers concentrations can be determined by other means as available by technical methods equivalent to ELISA. For means by which the biomarkers may be assessed known and emerging, biomarkers and algorithms additionally apply and can be leveraged for applications defined herein. For example, instantaneous measurements can be made to immediately assess a patient biomarker levels.

The test and biomarkers can be performed at any time, including but not limited to before a seizure, after a seizure, during a seizure, during a period of no seizures, during a period of multiple seizures, during a period of drug controlled seizures, and during a period of drug refractory seizures. The test can be performed at any time on any patients or individuals, including not limited, to be diagnosed epilepsy patients, drug controlled epilepsy patients and drug refractory patients. The test score and biomarkers can be analyzed and compared across patients, patient groups, other indications and normal controls, and across an individual patient over time for personalized medicine.

Systems, Software, Instruments, and Computers

The predictive models can be manually or automatically performed using software engineered for performing such a task. The analysis of concentrations of selected biomarkers may be performed manually or alternatively the analysis may be performed using software engineered for performing such a task. In preferred embodiments, an algorithm forms part of a predictive method of the present invention analyzes the concentrations of the selected biomarkers to present the diagnostic result or score. The algorithm may be performed manually or automatically via software engineered. The software engineered may be part of the instrument reading the concentrations of the selected biomarkers or may be part of an external computer. In other embodiments, the aforementioned software is loaded onto a computer. The computer also interfaces with the instrument inputs data directly from the instrument either manually or automatically. Individual measurements may be taken and analyzed individually or in any combination using linear or logarithmic units, or by using ratios of linear or logarithmic units, with and/or without patient demographic characteristics. The reciprocals of ratios of linear or logarithmic units may also be used. In some embodiments, the computer belongs to the end user, while in other embodiments, the computer or processor is provided as part of the kit. In preferred embodiments, the software engineered directs the computer to (a) access a file containing data from the instrument and (b) analyze these data using an algorithm of the invention. In other embodiments, the software engineered presents the results in a user-friendly format for interpreting the diagnostic results.

In some embodiments, methods and systems of the invention, can be embodied as a computer implemented process or processes for performing such computer-implemented process or processes, and can also be embodied in the form of a tangible storage medium (i.e., non-transitory computer readable medium) containing a computer program or other machine-readable instructions (herein "computer program"), wherein when the computer program is loaded into a computer or other processor (herein "computer") and/or is executed by the computer, the computer becomes an apparatus for practicing the process or processes. Storage media for containing such computer program include, for example, floppy disks and diskettes, compact disk (CD)-ROMs (whether or not writeable), DVD digital disks, RAM and ROM memories, computer hard drives and back-up drives, external hard drives, solid state drives, "thumb" drives, and any other storage medium readable by a computer. The process or processes can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the process or processes. The process or processes may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation.

Figure 12:
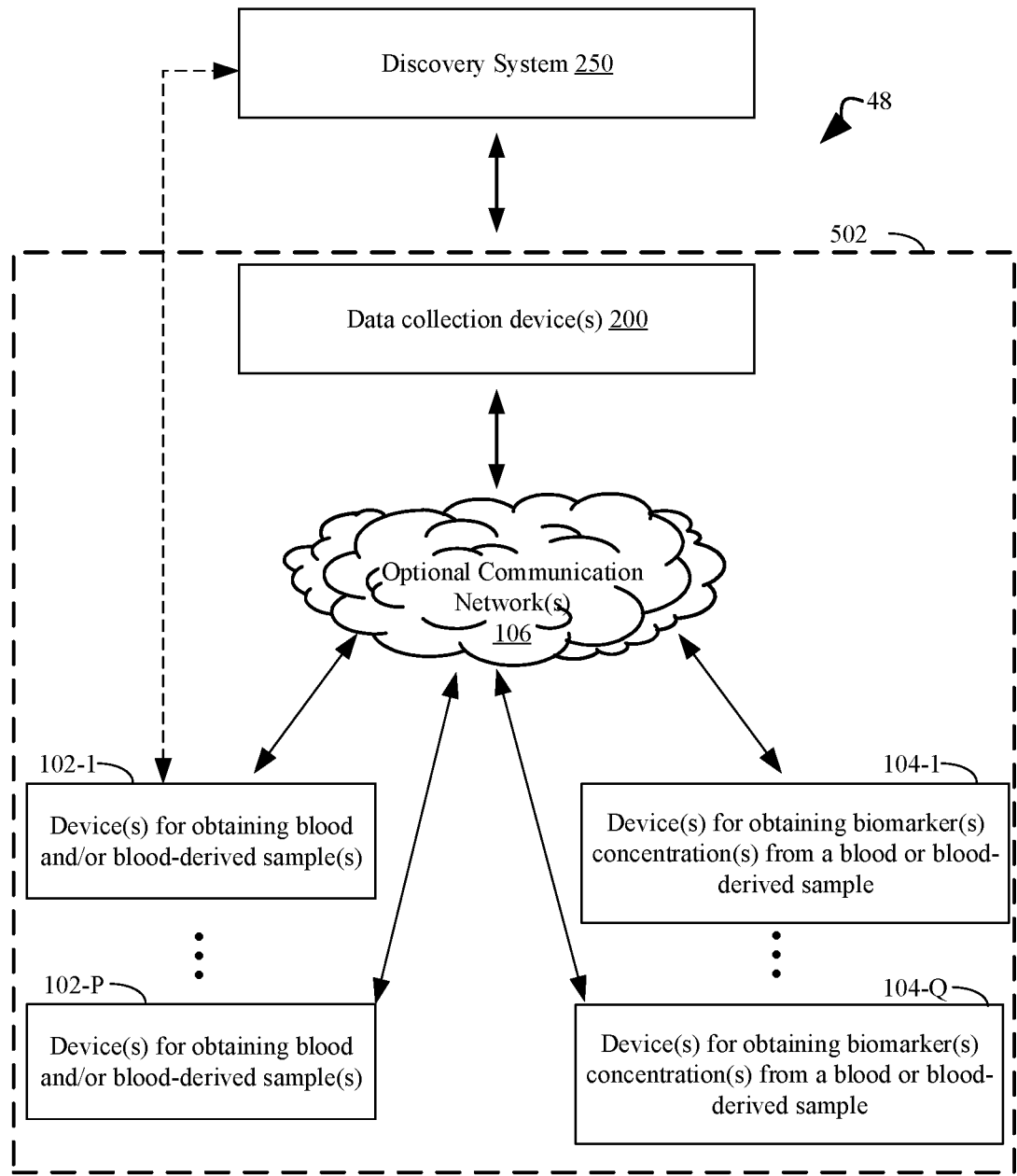
FIG. 12 illustrates an exemplary system topology for a system for screening a subject to determine the likelihood that the subject will be responsive to a treatment regimen that comprises administering to the subject an epilepsy therapeutic agent, in accordance with an embodiment of the present disclosure.
Figure 13:
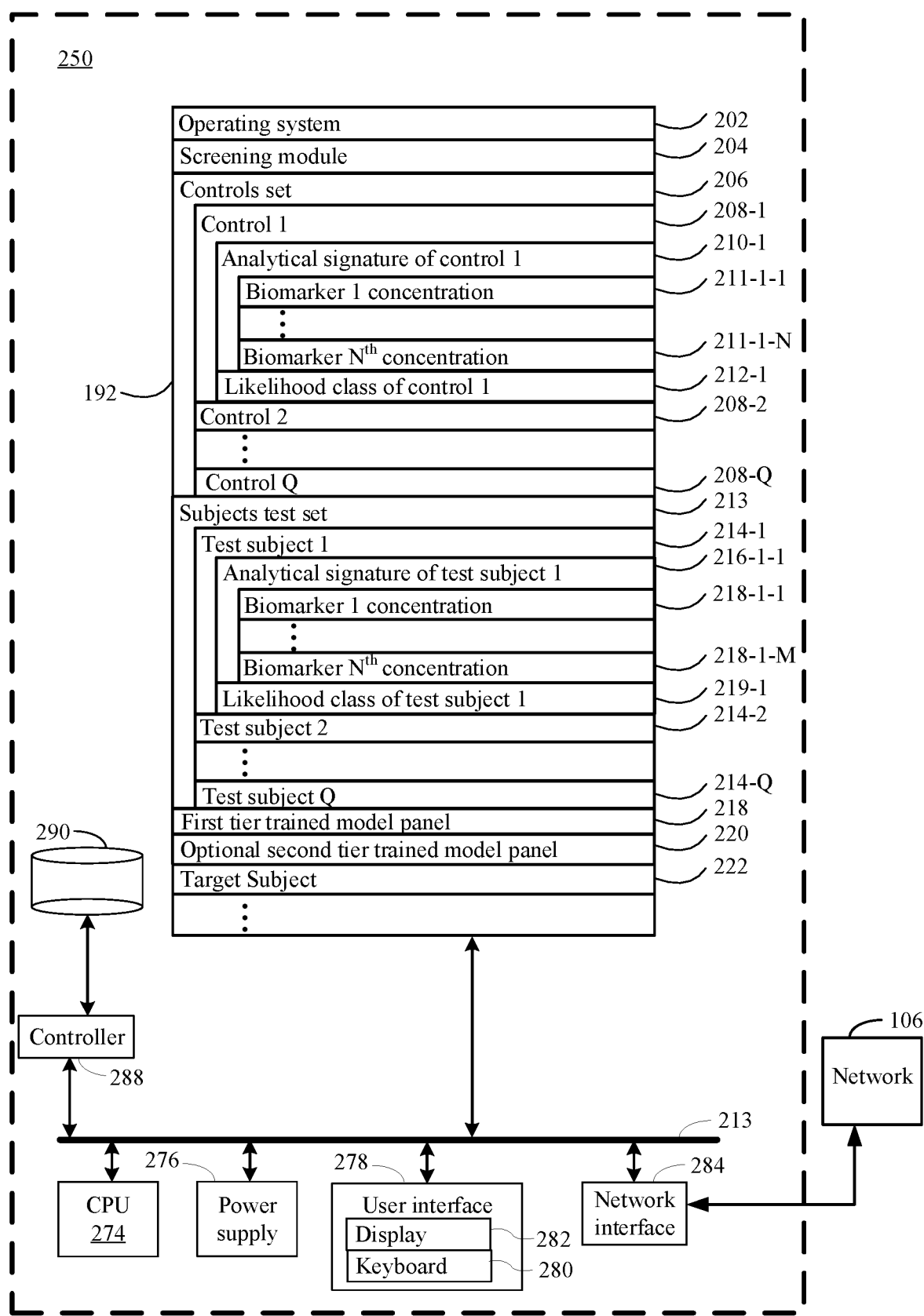
FIG. 13 illustrates an exemplary system for screening a subject to determine the likelihood that the subject will be responsive to a treatment regimen that comprises administering to the subject an epilepsy therapeutic agent, in accordance with an embodiment of the present disclosure.
Figure 14:
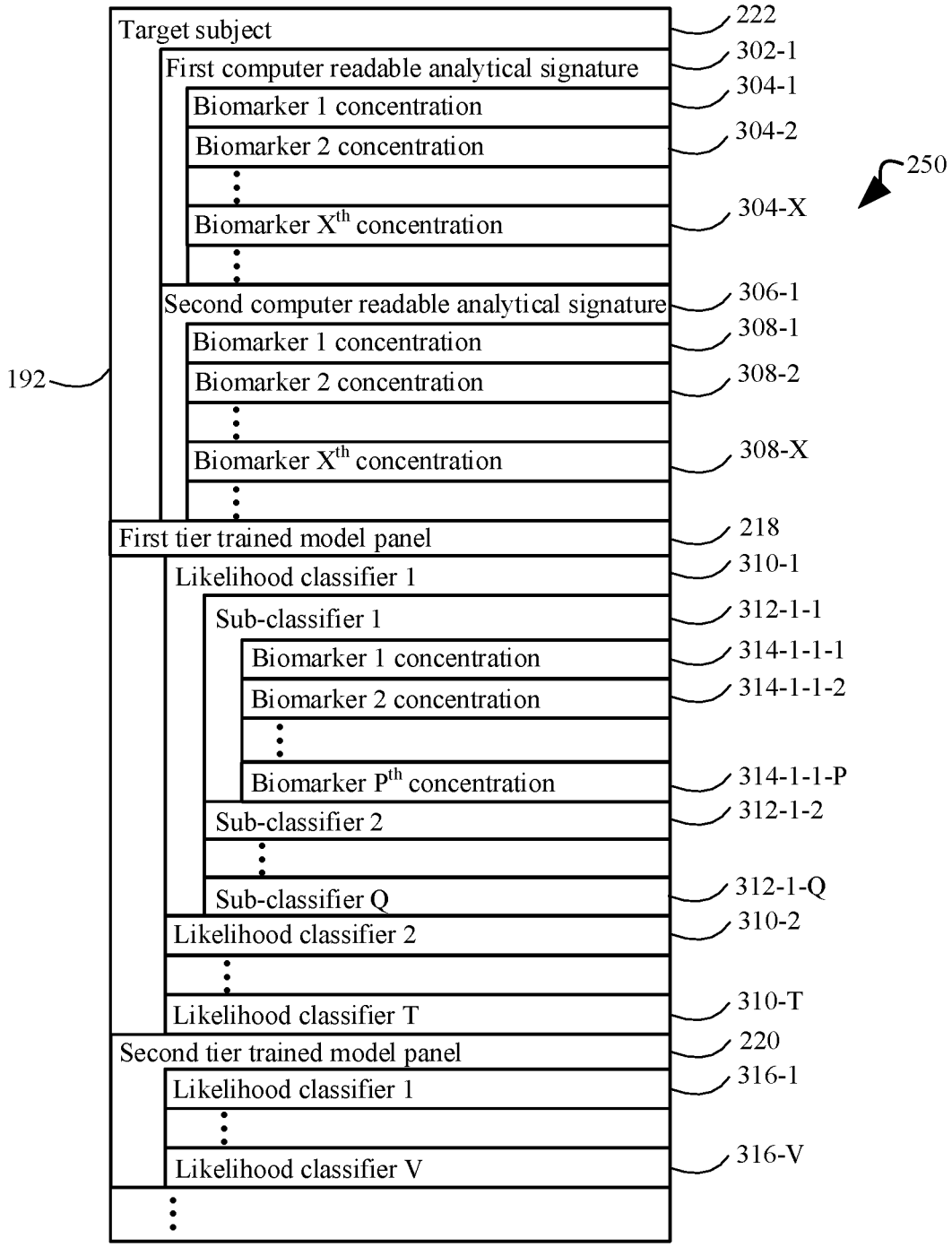
FIG. 14 illustrates exemplary data structures, in accordance with an embodiment of the present disclosure.

A detailed description of a system 48 for screening a subject to determine the likelihood that the subject will be responsive to a treatment regimen including administering epilepsy therapeutic agents is described in conjunction with FIGS. 12, 13, and 14. As such, FIGS. 12 through 14 collectively illustrate the topology of the system in accordance with the present disclosure. In the topology, there is a discovery system for screening a subject to determine whether it has a likelihood to respond to treatment ("discovery system 250") (FIGS. 12 and 13), one or more data collection devices 200, devices for obtaining blood and/or blood-derived samples 102, and devices for obtaining computer readable analytical signatures, for example biomarkers concentrations, from such samples 104 (FIG. 12). Throughout the present disclosure, the data collection devices 200 and the discovery system 250 will be referenced as separate devices solely for purposes of clarity. That is, the disclosed functionality of the data collection device 200 and the disclosed functionality of the discovery system 250 are contained in separate devices as illustrated in FIG. 12. However, it will be appreciated that, in fact, in some embodiments, the disclosed functionality of the one or more data collection devices 200 and the disclosed functionality of the discovery system 250 are contained in a single device. Likewise, in some embodiments, the data collection device 200 and the devices for obtaining blood and/or blood-derived samples 102 and/or the devices for obtaining computer readable analytical signatures from such samples 104 are the same devices. As described herein, the disclosed systems are equally applicable for i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

Referring to FIG. 12, the discovery system 250 screens a subject for the likelihood that the subject will be responsive to a treatment regimen including administering epilepsy therapeutic agents. To do this, the data collection device 200, which is in electrical communication with the discovery system 250, A) acquires a first computer readable analytical signature from a sample of the subject, for example a biomarker concentration, B) inputs the first computer readable analytical signature of the subject into a trained model panel of controls thereby obtaining a first trained model output value for the subject, and C) classifies the subject based upon the first trained model output value with a likelihood class in an enumerated set of likelihood classes. Each respective likelihood class in the enumerated set of likelihood classes is associated with a different likelihood that the subject will respond to the treatment regimen. Moreover, the likelihood includes a discernable effect of providing an epilepsy therapeutic agent to the subject classified with a likelihood class. In some embodiments, the subject has suffered one or more seizures. In some embodiments, the subject has suffered one seizure. In some embodiments, the subject has suffered two seizures. In some embodiments, the subject is a human subject.

In some embodiments, the data collection device 200 receives such data directly from the device(s) 102 and the device(s) 104. For instance, in some embodiments the data collection device 200 receives this data wirelessly through radio-frequency signals. In some embodiments such signals are in accordance with an 802.11 (Wi-Fi), Bluetooth, Zig-Bee, or by RFID communication. In some embodiments, the data collection device 200 receives such data directly, analyzes the data, and passes the analyzed data to the discover system 250. In some embodiments, the data collection device 200 and/or the discovery system 250 is not proximate to the devices 102 and/or devices 104 and/or does not have direct wireless capabilities or such wireless capabilities are not used for the purpose of acquiring data. In such embodiments, a communication network 106 may be used to communicate measurements of the first computer readable analytical signature (and/or second computer readable analytical signatures) from the devices 102 and the devices 104 to the data collection device 200 and/or the discovery system 250. Examples of networks 106 include, but are not limited to, the World Wide Web (WWW), an intranet and/or a wireless network, such as a cellular telephone network, a local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Other topologies of the system 48 are possible. For instance, rather than relying on a communications network 106, the one or more devices 102 and the one or more devices 104 may wirelessly transmit information directly to the data collection device 200 and/or discovery system 250. Further, the data collection device 200 and/or the discovery system 250 may constitute a portable electronic device, a server computer, or in fact constitute several computers that are linked together in a network or be a virtual machine in a cloud computing context. As such, the exemplary topology shown in FIG. 12 merely serves to describe the features of an embodiment of the present disclosure in a manner that will be readily understood to one of skill in the art.

Referring to FIG. 13, in typical embodiments, the discovery system 250 comprises one or more computers. For purposes of illustration in FIG. 13, the discovery system 250 is represented as a single computer that includes all of the functionality for screening a subject to determine its likelihood to respond to the treatment regimen. However, the disclosure is not so limited. In some embodiments, the functionality for screening a subject to determine whether it has a likelihood to respond to treatment, a likelihood to have a seizure, a likelihood to need treatment, a likelihood to respond to specific therapeutic agents, or a likelihood to adjust dosage pf a therapeutic agent, is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 13 with the foregoing in mind, an exemplary discovery system 250 for screening a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the discovery system 250 but that can be electronically accessed by the discovery system 250 over an Internet, intranet, or other form of network or electronic cable (illustrated as element 106 in FIG. 13) using network interface 284. As described herein, screening can be done as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, the memory 192 of the discovery system 250 for screening a subject, stores:
- an operating system 202 that includes procedures for handling various basic system services;
- a screening module 204 for screening a subject to determine whether it is likely to respond to epilepsy treatment;
- a controls set 206 that comprises one or more controls 208, each control comprising one or more analytical signatures 210, for each respective analytical signature, (i) one or more biomarkers concentrations from a sample from a training control entity and (ii) a likelihood class 212 of the training control entity 208;
- a test set 213 that comprises an analytical signature 216 for each test subject 214 in a plurality of test subjects and, for each respective analytical signature 216, (i) one or more biomarker concentrations 218 obtained from a sample from the corresponding test subject and (ii) a likelihood class 219 of the test subject 214;
- a first tier trained model panel 218 for screening a subject to determine whether it is likely to respond to epilepsy treatment;
- an optional second tier trained model panel 220 for screening a subject to determine whether it is likely to respond to epilepsy treatment; and
- data for a target subject 222 including an analytical signature for the target subject.

In some embodiments, the screening module 204 is accessible within any browser (phone, tablet, laptop/desktop). In some embodiments, the screening module 204 runs on native device frameworks, and is available for download onto the discovery system 250 running an operating system 202 such as Android or iOS.

In some embodiments, the controls set 206 is referenced in FIG. 2. In some embodiments, the subjects test set 213 is referenced in FIG. 2.

In some embodiments, the first tier trained model panel consists of a single support vector machine. In some embodiments, the first tier trained model panel consists of a plurality of support vector machines.

In some embodiments, the biomarkers are selected from Table 2. In some embodiments, the biomarkers are selected from the group consisting of one biomarker, two biomarkers, and three biomarkers. In some embodiments, the biomarkers are selected from the group consisting of IL-16, TARC, and TNF-alpha. In some embodiments, the biomarker is IL-16. In some embodiments, the biomarker is TARC. In some embodiments, the biomarker is TNF-alpha. In some embodiments, the two biomarkers are IL-16 and TARC. In some embodiments, the two biomarkers are IL-16 and TNF-alpha. In some embodiments, the two biomarkers are TARC and TNF-alpha. In some embodiments, the three biomarkers are IL-16, TARC, and TNF-alpha. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one or more seizures. In some embodiments, the subject has suffered one seizure. In some embodiments, the subject has suffered two seizures. In some embodiments, the subject has never suffered seizures.

In some embodiments, a program described herein further comprises instructions for: training, prior to the comparing, one or more models to thereby form a first tier trained model. In some embodiments, the training comprises: obtaining a training set that represents a plurality of training subjects, wherein some training subjects in the plurality of training subjects have epilepsy and, for each respective training subject, the training set comprises (i) a computer readable analytical signature from a sample of the respective training subject and (ii) an effect that providing an epilepsy therapeutic agent had on epilepsy, and using the training set to train the one or more models thereby forming the first tier trained model panel. In some embodiments, the enumerated set of classes comprises i) likely to respond to treatment, and ii) unlikely to respond to treatment. In some embodiments, the enumerated set of classes consists of i) likely to respond to treatment, and ii) unlikely to respond to treatment. In some embodiments, the enumerated set of classes comprises i) likely to have a seizure, and ii) unlikely to have a seizure. In some embodiments, the enumerated set of classes consists of i) likely to have a seizure, and ii) unlikely to have a seizure. In some embodiments, the enumerated set of classes comprises i) likely to need treatment, and ii) unlikely to need treatment. In some embodiments, the enumerated set of classes consists of i) likely to need treatment, and ii) unlikely to need treatment. In some embodiments, the enumerated set of classes comprises i) likely to need specific therapeutic agent, and ii) unlikely to need specific therapeutic agent. In some embodiments, the enumerated set of classes consists of i) likely to need specific therapeutic agent, and ii) unlikely to need specific therapeutic agent. In some embodiments, the enumerated set of classes comprises i) likely to need therapeutic agent dosage change, and ii) unlikely to need therapeutic agent dosage change. In some embodiments, the enumerated set of classes consists of i) likely to need therapeutic agent dosage change, and ii) unlikely to need therapeutic agent dosage change. In some embodiments, the training set comprises a different plurality of training subjects for each class in the enumerated set of classes. In some embodiments, the training set comprises: a first subset of subjects that have been provided epilepsy treatment and responded to treatment, and a second subset of subjects that have been provided epilepsy treatment and did not respond to treatment. In some embodiments, the training set comprises: a first subset of subjects that had past seizures, and a second subset of subjects that did not have past seizures. In some embodiments, the training set comprises: a first subset of subjects that had past treatment, and a second subset of subjects that did not have past treatment. In some embodiments, the treatment regimen comprises administering to the subject one or more therapeutic agents selected from the following group including, but not limited to, the group consisting of phenytoin, fosphenytoin, midazolam, pregabalin, acetazolamide, methsuximide, ethotoin, piracetam, nitrazepam, paraldehyde, stiripentol, vigabatrin, brivaracetam, perampanel, rufinamide, lurasidone HCl, carbamazepine, clobazam, clonazepam, diazepam, divalproex, eslicarbazepine acetate, ethosuximide, ezogabine, felbamate, gabapentin, lacosamide, lamotrigine, levetiracetam, lorazepam, oxcarbazepine, phenobarbital, primidone, tiagabine, topiramate, valproic acid, zonisamide, cannabis-based drugs, and pharmaceutically acceptable salts, prodrugs, and derivatives thereof. In some embodiments, the subject has suffered one seizure. In some embodiments, the subject has suffered two seizures. In some embodiments, the subject is a human subject.

Referring to FIG. 14, in some embodiments, the target subject 222 has a first computer readable analytical signature 302 that comprises one or more biomarkers concentrations 304. For instance, in some embodiments, the first computer readable analytical signature 302 comprises one or more biomarker concentrations for one or more biomarkers provided in Table 2. In some embodiments, the target entity 222 has a second computer readable analytical signature 306 that comprises a separate biomarker concentration 308.

As described herein in reference to Table 2, in some embodiments, a biomarker concentration can be in a range defined as (mean value–standard deviation) to (mean value+standard deviation). For example, in some embodiments, a biomarker concentration described in Table 2 as subject (or patient) biomarker concentration, can be in a range from (seizure patient mean–seizure standard deviation) to (seizure patient mean+seizure standard deviation). In some embodiments, a biomarker concentration described in Table 2 as control biomarker concentration, can be in a range from (control mean–control standard deviation) to (control mean+control standard deviation).

Referring to FIG. 14, in some embodiments, the likelihood classifier 310 is a single classifier. In some alternative embodiments, the likelihood classifier 310 is a composite of a plurality of sub-classifiers 312. In such embodiments, each sub-classifier 312 comprises, as input, a select biomarker concentration 314 (subsets). For instance, in some embodiments each biomarker concentration 314 corresponds to one or two of the subset ranges 304 of the first computer readable analytical signature. In some embodiments each likelihood classifier is trained using a different subset of the training controls set 206. As described herein, likelihood refers to one or more of likely to respond to treatment, unlikely to respond to treatment, likely to have a seizure, unlikely to have a seizure, likely to need treatment, unlikely to need treatment, likely to need specific therapeutic agent, unlikely to need specific therapeutic agent, likely to need therapeutic agent dosage change, and unlikely to need therapeutic agent dosage change.

In some embodiments, each likelihood classifier 310 is a nearest neighbor analysis against the subjects test set 213. That is, select biomarker concentrations subset ranges in an analytical signature from a target subject 222 serve as input into the first tier trained model panel 218 and/or second tier trained model panel 220 and nearest neighbor analysis is used to determine the most similar subjects in the test set 212 to the target subject 222. Then, the likelihood class of these most similar test subjects are polled and combined to form the likelihood class called by the first tier trained model panel 218 and/or second tier trained model panel 220 for the target subject 222.

In some embodiments, each likelihood classifier 310 is panel of nearest neighbor analyses against the subjects test set 213. In such embodiments, each nearest neighbor analysis in the panel is a sub-classifier 312. In such embodiments, select biomarker concentrations ranges 314 in an analytical signature 302/306 from the target subject 222 serve as input into each sub-classifier 312 and nearest neighbor analysis is used by each sub-classifier 312 to determine the most similar entities in the subjects test set 213 to the target subject 222. Then, the likelihood class of these most similar test subjects are polled and combined to form the likelihood class called by each respective likelihood classifier 310 for the target entity 222.

In some embodiments, the first trained model panel 218 and/or second trained model panel 218 is an artificial neural network. In some embodiments, the first trained model panel 218 and/or second trained model panel 218 is linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification*, Second Edition, John Wiley & Sons, Inc., New York; Hastie, 2003, The Elements of Statistical Learning, Springer, New York; and Agresti 1996, *An Introduction to Categorical Data Analysis*, John Wiley & Sons, New York, each of which is hereby incorporated by reference herein for such purpose.

In some embodiments, the first trained model panel 218 and/or second trained model panel 218 comprises a plurality of sub-classifiers 312 and each respective sub-classifier is an artificial neural network. In some embodiments, the first trained model panel 218 and/or second trained model panel 218 comprises a plurality of sub-classifiers 312 and each respective sub-classifier is a linear regression, non-linear regression, logistic regression, multivariate data analysis, classification using a regression tree, partial least squares projection to latent variables, computation of a neural network, computation of a Bayesian model, computation of a generalized additive model, use of a support vector machine, or modeling comprising boosting or adaptive boosting. See, for example, Duda et al., 2001, *Pattern Classification, Second Edition*, John Wiley & Sons, Inc., New York; Hastie, 2003, The Elements of Statistical Learning, Springer, New York; and Agresti 1996, *An Introduction to Categorical Data Analysis*, John Wiley & Sons, New York, each of which is hereby incorporated by reference herein for such purpose. In such embodiments, the sub-classifiers are combined to form a final value for the respective first trained model panel 218 and/or second trained model panel 218.

In some implementations, one or more of the above identified data elements or modules of the discovery system 250 for screening a target subject to determine whether it is likely to respond to epilepsy treatment are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above. As described herein, screening a subject can be done as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, a discovery system 250 for screening a target subject to determine whether it is likely to respond to epilepsy treatment is a smart phone (e.g., an iPhone), laptop, tablet computer, desktop computer, or other form of electronic device (e.g., a gaming console). In some embodiments, the discovery system 250 is not mobile. In some embodiments, the discovery system 250 is mobile.

In some embodiments the discovery system 250 is a tablet computer, desktop computer, or other form or wired or wireless networked device. In some embodiments, the discovery system 250 has any or all of the circuitry, hardware components, and software components found in the discovery system 250 depicted in FIG. 12 or 13. In the interest of brevity and clarity, only a few of the possible components of the discovery system 250 are shown in order to better emphasize the additional software modules that are installed on the discovery system 250.

Now that details of a system 48 for screening a target subject to determine its likelihood to respond to epilepsy treatment have been disclosed, details regarding aspects of methods for screening a target subject to determine whether it is likely to respond to epilepsy treatment are disclosed below. As described herein, screening a subject can be done as part of any number of methods, i.e.: i) methods of screening a subject to determine the likelihood that the subject will have a seizure in the future; ii) methods of screening the likelihood that a subject needs to begin a treatment regimen; iii) methods of screening the likelihood that the subject needs an adjustment, for example an increase, in a treatment regimen or therapeutic agent dosage; and/or iv) methods for selecting a specific therapeutic agent as being more effective than other therapeutic agents in a treatment regimen for epileptic seizures. As described herein, the methods are equally applicable to subjects that never had a seizure in the past, subjects that had one or more seizures in the past, subjects that received treatment for epileptic seizures in the past, and subjects that never received treatment for epileptic seizures in the past. In some embodiments, the subject is a human subject.

In some embodiments, device 104 obtains abundance, levels, or concentrations of biomarkers to be quantified in plasma by any of a number of methods known in the art, the particular procedure not being a limitation of the embodiments herein. In some embodiments the analytical signature 210 of a control 208, the analytical signature 216 of a test subject 214, and/or the analytical signature 302 or 306 of a target subject is acquired using any method known in the art. For example, ELISA, Indirect ELISA, Sandwich ELISA, Competitive Elisa, and Multiple and Portable (M&P) ELISA may be used. Probes specific to the antigen (polypeptide or marker) to be detected may be obtained commercially or designed by techniques known in the art, and a variety of capture and detect antibodies may be used to detect biomarkers by those skilled in the art. Single- and multi-probe kits are available from commercial suppliers, e.g., Meso Scale Discovery. These kits include the kits referenced in the Examples hereto. Individual measurements may be taken and analyzed individually or in any combination using linear or logarithmic units, or by using ratios of linear or logarithmic units. The reciprocals of ratios of linear or logarithmic units may also be used.

EXAMPLES

Reference is now made to the following examples, which, together with the above descriptions, illustrate certain embodiments of the invention in a non-limiting fashion. These examples are provided for the purpose of illustration only and the disclosure encompassed herein should in no way be construed as being limited to these examples, but rather should be construed to encompass any and all variations which become evident as a result of the teachings provided herein.

Example 1: Patient Demographics and Biomarker Data: Inpatients, Outpatients and Normal Controls Patient demographics are defined in Table 1. The demographics indicate the total number of patients, the number of samples taken, and the average age for each group, and also indicate the fraction of patients in each category. Biomarkers analyzed with key diagnostic parameters are shown in Tables 2 and 3. These biomarkers can be used alone or in combination for the determination of seizure or not and epilepsy or not. Additionally, these biomarkers serve as the basis for the algorithm determination.

TABLE 1

Patient Demographics

|  |  | Evogen Seizure | Evogen Control |
|---|---|---|---|
|  | Patients | 23 | 29 |
|  | Samples | 31 | 29 |
| Age (%) | <18 | 0 | 0 |
|  | 18-29 | 21.7 | 20.7 |
|  | 30-44 | 34.8 | 10.3 |
|  | 45-59 | 30.4 | 20.7 |
|  | >59 | 13.0 | 48.3 |
| Gender (%) | Male | 34.8 | 31 |
|  | Female | 65.2 | 69 |
| Race (%) | White | 60.9 | ND |
|  | Black | 26.1 |  |
|  | Asian | 0.0 |  |
|  | Unknown | 13.0 |  |
| # of AEDs (%) | 0 | 8.7 | 100 |
|  | 1 | 21.7 | 0 |
|  | 2 | 34.8 | 0 |
|  | 3+ | 34.8 | 0 |
| Seizure Classification (%) | Focal | 87.0 | 0 |
|  | Generalized | 13.0 | 0 |
| Seizure Frequency | Average | 5.62 | 0 |

TABLE 2

Biomarker concentrations, p-values and diagnostic ability for each biomarker.

| Biomarker | Seizure Patient Mean | Seizure Standard deviation | Control Mean | Control Standard Deviation | P-value | P val std | AUC | Sensitivity | Specificity |
|---|---|---|---|---|---|---|---|---|---|
| IL-16 | 166.5984 | 65.58077 | 274.9017 | 135.5053 | 0.000242 | 0.010916 | 0.768632 | 0.645161 | 0.827586 |
| TARC | 183.2173 | 183.8669 | 64.12069 | 50.21182 | 0.00158 | 0.026255 | 0.647942 | 0.419355 | 0.965517 |
| TRAIL | 222.5935 | 106.6664 | 308.9655 | 103.3498 | 0.00275 | 0.080281 | 0.740267 | 0.677419 | 0.793103 |
| IL-7 | 8.272677 | 7.642648 | 3.760897 | 3.918483 | 0.006925 | 0.082654 | 0.696329 | 0.612903 | 0.758621 |
| MCP-4 | 120.9161 | 83.81586 | 73.80345 | 50.7786 | 0.012835 | 0.135705 | 0.666852 | 0.516129 | 0.896552 |
| P-Cadherin | 17545.48 | 6341.123 | 22125.34 | 7798.423 | 0.016861 | 0.152978 | 0.689099 | 0.483871 | 0.862069 |
| Osteoactivin | 19970.97 | 4812.078 | 23186.21 | 5254.258 | 0.018106 | 0.152727 | 0.6802 | 0.387097 | 0.931034 |
| M-CSF | 25.52 | 19.13737 | 15.22207 | 12.91711 | 0.020333 | 0.134499 | 0.756952 | 0.709677 | 0.758621 |
| ICAM-1 | 379290.3 | 76318.49 | 432844.8 | 98690.14 | 0.023872 | 0.163636 | 0.644605 | 0.516129 | 0.758621 |
| MMP-3 | 9545 | 6054.744 | 13086.21 | 5581.165 | 0.024384 | 0.1852 | 0.71802 | 0.451613 | 0.965517 |
| MCP-2 | 29.42726 | 16.63736 | 21.50172 | 11.17995 | 0.038756 | 0.190824 | 0.625695 | 0.451613 | 0.896552 |
| IL-8 | 8.70129 | 7.612402 | 5.842069 | 1.925489 | 0.058286 | 0.131527 | 0.603448 | 0.290323 | 1 |
| Osteonectin | 129272.6 | 109324.4 | 83806.9 | 64432.58 | 0.060695 | 0.206348 | 0.594549 | 0.483871 | 0.793103 |
| SAA | 35317419 | 83253974 | 5844862 | 4343100 | 0.066256 | 0.094565 | 0.581201 | 0.290323 | 0.965517 |
| MIP-1B | 73.61935 | 28.7821 | 57.28448 | 37.6091 | 0.067308 | 0.254975 | 0.753615 | 0.709677 | 0.793103 |
| TNF-a | 2.328677 | 1.276182 | 2.895345 | 1.092999 | 0.075399 | 0.235729 | 0.693548 | 0.451613 | 0.931034 |
| CRP | 15798371 | 33915272 | 4272276 | 3488016 | 0.078585 | 0.077442 | 0.602336 | 0.290323 | 1 |
| MIF | 78048.47 | 71757.34 | 49578.24 | 63928.39 | 0.116958 | 0.268308 | 0.619021 | 0.419355 | 0.896552 |
| IL-5 | 0.456881 | 0.434237 | 0.609595 | 0.335793 | 0.141351 | 0.273919 | 0.688543 | 0.548387 | 0.827586 |
| TNF-B | 0.206594 | 0.126409 | 0.24451 | 0.079655 | 0.180315 | 0.290246 | 0.62792 | 0.774194 | 0.517241 |
| Nectin-4 | 1084.726 | 330.4005 | 979.8276 | 326.9187 | 0.229495 | 0.295959 | 0.613459 | 0.580645 | 0.758621 |
| Eotaxin | 125.55 | 54.26923 | 149.0879 | 96.43018 | 0.252857 | 0.283362 | 0.53337 | 0.741935 | 0.413793 |
| MCP-1 | 93.81774 | 28.77321 | 101.5517 | 21.59106 | 0.254139 | 0.293433 | 0.602892 | 0.580645 | 0.724138 |
| MIP-5 | 7458.387 | 1825.985 | 6872.241 | 2157.029 | 0.267601 | 0.295834 | 0.629032 | 0.709677 | 0.689655 |
| IL-10 | 0.394606 | 0.27393 | 1.422448 | 5.081076 | 0.273445 | 0.208827 | 0.471635 | 1 | 0.068966 |
| Calbindin | 251.8194 | 105.1653 | 279.931 | 104.0485 | 0.310766 | 0.303115 | 0.600667 | 0.483871 | 0.724138 |
| MIP-1a | 16.30032 | 6.153641 | 86.78446 | 378.0642 | 0.31176 | 0.219064 | 0.446607 | 1 | 0.034483 |
| IL-12/IL-23p40 | 130.5661 | 73.31145 | 145.6741 | 52.37085 | 0.373063 | 0.302789 | 0.586763 | 0.483871 | 0.827586 |
| IL-15 | 2.878387 | 0.852934 | 2.70931 | 0.580592 | 0.384307 | 0.293914 | 0.528365 | 0.322581 | 0.862069 |
| VCAM-1 | 589516.1 | 158984.6 | 556689.7 | 123723 | 0.386022 | 0.300554 | 0.571746 | 0.548387 | 0.655172 |
| IL-17A | 1.642516 | 1.205362 | 2.134517 | 3.264801 | 0.444007 | 0.258157 | 0.535039 | 0.290323 | 0.896552 |
| SCF | 41.65484 | 15.86248 | 44.51897 | 12.33001 | 0.447884 | 0.306359 | 0.566741 | 0.290323 | 0.931034 |
| IL-1a | 10.86742 | 32.72898 | 19.23776 | 52.08565 | 0.463668 | 0.302541 | 0.585651 | 0.935484 | 0.310345 |
| Cytokeratin-8 | 10483.23 | 13064.89 | 8425.172 | 9701.944 | 0.500834 | 0.292131 | 0.55673 | 0.451613 | 0.689655 |
| Eotaxin-2 | 1487.097 | 1292.314 | 1302.948 | 968.9888 | 0.543746 | 0.292155 | 0.542269 | 0.548387 | 0.724138 |
| VEGF-A | 67.72419 | 48.7806 | 77.82069 | 85.93546 | 0.581243 | 0.284705 | 0.511123 | 1 | 0.068966 |
| MMP-9 | 55841.94 | 34174.26 | 59468.97 | 26759.53 | 0.655847 | 0.301272 | 0.596774 | 0.645161 | 0.551724 |
| MMP-1 | 1978.323 | 2184.419 | 2139.414 | 2429.157 | 0.791285 | 0.287638 | 0.478309 | 0.064516 | 1 |
| TNF-RI | 2270.484 | 647.6812 | 2230.172 | 861.5128 | 0.840439 | 0.296031 | 0.605673 | 0.741935 | 0.448276 |
| MDC | 1054.71 | 455.7338 | 1072.741 | 399.9249 | 0.87366 | 0.292795 | 0.503893 | 0.096774 | 0.965517 |
| TNF-RII | 3629.032 | 1241.723 | 3685.172 | 1634.776 | 0.882976 | 0.290002 | 0.453838 | 1 | 0.103448 |
| IP-10 | 351.1468 | 420.0991 | 345.0517 | 175.5184 | 0.943466 | 0.31448 | 0.515017 | 0.032258 | 1 |
| Eotaxin-3* | 0.903226 | 0.29565 | 0.931034 | 0.253395 | 0.104258 | 0.140911 | 0.513904 | 0.096774 | 0.931034 |
| GM-CSF* | 0.83871 | 0.367799 | 0.724138 | 0.446948 | 0.310881 | 0.270109 | 0.557286 | 0.83871 | 0.275862 |
| IFN-y* | 0.903226 | 0.29565 | 0.931034 | 0.253395 | 0.323448 | 0.223233 | 0.513904 | 0.096774 | 0.931034 |
| IL-12p70* | 0.645161 | 0.478464 | 0.551724 | 0.497317 | 0.411491 | 0.301696 | 0.546719 | 0.645161 | 0.448276 |
| IL-13* | 0.225806 | 0.418112 | 0.344828 | 0.475312 | 0.43659 | 0.272645 | 0.559511 | 0.774194 | 0.344828 |
| IL-1B* | 0.290323 | 0.453911 | 0.103448 | 0.304543 | 0.411115 | 0.319635 | 0.593437 | 0.290323 | 0.896552 |
| IL-2* | 0.806452 | 0.395079 | 0.862069 | 0.344828 | 0.354711 | 0.29265 | 0.527809 | 0.193548 | 0.862069 |
| IL-4* | 0.225806 | 0.418112 | 0.241379 | 0.42792 | 0.503227 | 0.289098 | 0.507786 | 0.774194 | 0.241379 |
| IL-6* | 0.967742 | 0.176685 | 1 | 0 | 0.268892 | 0.208761 | 0.516129 | 0.032258 | 1 |

*indicates biomarkers that were used as binary classifiers of detectable levels
**all values reported in pg/mL, except binary classificiers

TABLE 3

Biomarker concentrations, p-values and diagnostic ability for each biomarker, including scaled biomarker concentrations

| Biomarker | Seizure Patient Mean | Seizure Standard deviation | Control Mean | Control Standard Deviation | P-value | P val std | AUC | Sensitivity | Specificity |
|---|---|---|---|---|---|---|---|---|---|
| Calbindin | 251.8194 | 105.1653 | 279.931 | 104.0485 | 0.310766 | 0.301982 | 0.600667 | 0.483871 | 0.7241379 |
| CRP | 15798371 | 33915272 | 4272276 | 3488016 | 0.078585 | 0.082109 | 0.602336 | 0.290323 | 1 |
| Cytokeratin-8 | 10483.23 | 13064.89 | 8425.172 | 9701.944 | 0.500834 | 0.294042 | 0.55673 | 0.451613 | 0.6896552 |
| Eotaxin | 125.55 | 54.26923 | 149.0879 | 96.43018 | 0.252857 | 0.282147 | 0.53337 | 0.741935 | 0.4137931 |
| Eotaxin-2 | 1487.097 | 1292.314 | 1302.948 | 968.9888 | 0.543746 | 0.295118 | 0.542269 | 0.548387 | 0.7241379 |
| ICAM-1 | 379290.3 | 76318.49 | 432844.8 | 98690.14 | 0.023872 | 0.164246 | 0.644605 | 0.516129 | 0.7586207 |
| IL-10 | 0.394606 | 0.27393 | 1.422448 | 5.081076 | 0.273445 | 0.205803 | 0.471635 | 1 | 0.0689655 |
| IL-12/IL-23p40 | 130.5661 | 73.31145 | 145.6741 | 52.37085 | 0.373063 | 0.3064 | 0.586763 | 0.483871 | 0.8275862 |
| IL-15 | 2.878387 | 0.852934 | 2.70931 | 0.580592 | 0.384307 | 0.295171 | 0.528365 | 0.322581 | 0.862069 |

TABLE 3-continued

Biomarker concentrations, p-values and diagnostic ability for each biomarker, including scaled biomarker concentrations

| Biomarker | Seizure Patient Mean | Seizure Standard deviation | Control Mean | Control Standard Deviation | P-value | P val std | AUC | Sensitivity | Specificity |
|---|---|---|---|---|---|---|---|---|---|
| IL-16 | 166.5984 | 65.58077 | 274.9017 | 135.5053 | 0.000242 | 0.01322 | 0.768632 | 0.645161 | 0.8275862 |
| IL-17A | 1.642516 | 1.205362 | 2.134517 | 3.264801 | 0.444007 | 0.263023 | 0.535039 | 0.290323 | 0.8965517 |
| IL-1a | 10.86742 | 32.72898 | 19.23776 | 52.08565 | 0.463668 | 0.301236 | 0.585651 | 0.935484 | 0.3103448 |
| IL-5 | 0.456881 | 0.434237 | 0.609595 | 0.335793 | 0.141351 | 0.279809 | 0.688543 | 0.548387 | 0.8275862 |
| IL-7 | 8.272677 | 7.642648 | 3.760897 | 3.918483 | 0.006925 | 0.086123 | 0.696329 | 0.612903 | 0.7586207 |
| IL-8 | 8.70129 | 7.612402 | 5.842069 | 1.925489 | 0.058286 | 0.136838 | 0.603448 | 0.290323 | 1 |
| IP-10 | 351.1468 | 420.0991 | 345.0517 | 175.5184 | 0.943466 | 0.314503 | 0.515017 | 0.032258 | 1 |
| MCP-1 | 93.81774 | 28.77321 | 101.5517 | 21.59106 | 0.254139 | 0.29406 | 0.602892 | 0.580645 | 0.7241379 |
| MCP-2 | 29.42726 | 16.63736 | 21.50172 | 11.17995 | 0.038756 | 0.181286 | 0.625695 | 0.451613 | 0.8965517 |
| MCP-4 | 120.9161 | 83.81586 | 73.80345 | 50.7786 | 0.012835 | 0.132679 | 0.666852 | 0.516129 | 0.8965517 |
| M-CSF | 25.52 | 19.13737 | 12.91711 | 15.22207 | 0.020333 | 0.13309 | 0.756952 | 0.709677 | 0.7586207 |
| MDC | 1054.71 | 455.7338 | 1072.741 | 399.9249 | 0.87366 | 0.290874 | 0.503893 | 0.096774 | 0.9655172 |
| MIF | 78048.47 | 71757.34 | 49578.24 | 63928.39 | 0.116958 | 0.260561 | 0.619021 | 0.419355 | 0.8965517 |
| MIP-1a | 16.30032 | 6.153641 | 86.78466 | 378.0642 | 0.31176 | 0.222294 | 0.446607 | 1 | 0.0344828 |
| MIP-1B | 73.61935 | 28.7821 | 57.28448 | 37.6091 | 0.067308 | 0.256347 | 0.753615 | 0.709677 | 0.7931034 |
| MIP-5 | 7458.387 | 1825.985 | 6872.241 | 2157.029 | 0.267601 | 0.301967 | 0.629032 | 0.709677 | 0.6896552 |
| MMP-1 | 1978.323 | 2184.419 | 2139.414 | 2429.157 | 0.791285 | 0.286845 | 0.478309 | 0.064516 | 1 |
| MMP-3 | 9545 | 6054.744 | 13086.21 | 5581.165 | 0.024384 | 0.176426 | 0.71802 | 0.451613 | 0.9655172 |
| MMP-9 | 55841.94 | 34174.26 | 59468.97 | 26759.53 | 0.655847 | 0.298339 | 0.596774 | 0.645161 | 0.5517241 |
| Nectin-4 | 1084.726 | 330.4005 | 979.8276 | 326.9187 | 0.229495 | 0.297985 | 0.613459 | 0.580645 | 0.7586207 |
| Osteoactivin | 19970.97 | 4812.078 | 23186.21 | 5254.258 | 0.018106 | 0.153373 | 0.6802 | 0.387097 | 0.9310345 |
| Osteonectin | 129272.6 | 109324.4 | 83806.9 | 64432.58 | 0.060695 | 0.202338 | 0.594549 | 0.483871 | 0.7931034 |
| P-Cadherin | 17545.48 | 6341.123 | 22125.34 | 7798.423 | 0.016861 | 0.139423 | 0.689099 | 0.483871 | 0.862069 |
| SAA | 35317419 | 83253974 | 5844862 | 4343100 | 0.066256 | 0.097983 | 0.581201 | 0.290323 | 0.9655172 |
| SCF | 41.65484 | 15.86248 | 44.51897 | 12.33001 | 0.447884 | 0.304235 | 0.566741 | 0.290323 | 0.9310345 |
| TARC | 183.2173 | 183.8669 | 64.12069 | 50.21182 | 0.00158 | 0.02995 | 0.647942 | 0.419355 | 0.9655172 |
| TNF-RI | 2270.484 | 647.6812 | 2230.172 | 861.5128 | 0.840643 | 0.293801 | 0.605673 | 0.741935 | 0.4482759 |
| TNF-RII | 3629.032 | 1241.723 | 3685.172 | 1634.776 | 0.882976 | 0.286725 | 0.453838 | 1 | 0.1034483 |
| TNF-a | 2.328677 | 1.276182 | 2.895345 | 1.092999 | 0.075399 | 0.239402 | 0.693548 | 0.451613 | 0.9310345 |
| TNF-B | 0.206594 | 0.126409 | 0.24451 | 0.079655 | 0.180315 | 0.286534 | 0.62792 | 0.774194 | 0.5172414 |
| TRAIL | 222.5935 | 106.6664 | 308.9655 | 103.3498 | 0.00275 | 0.083458 | 0.740667 | 0.677419 | 0.7931034 |
| VCAM-1 | 589516.1 | 158984.6 | 556689.7 | 123723 | 0.386022 | 0.299573 | 0.571746 | 0.548387 | 0.6551724 |
| VEGF-A | 67.72419 | 48.7806 | 77.82069 | 85.93546 | 0.581243 | 0.2866 | 0.511123 | 1 | 0.0689655 |
| Eotaxin-3* | 0.903226 | 0.29565 | 0.931034 | 0.253395 | 0.104258 | 0.140911 | 0.513904 | 0.096774 | 0.9310345 |
| GM-CSF* | 0.83871 | 0.367799 | 0.724138 | 0.446948 | 0.310881 | 0.270109 | 0.557286 | 0.83871 | 0.2758621 |
| IFN-y* | 0.903226 | 0.29565 | 0.931034 | 0.253395 | 0.323448 | 0.223233 | 0.513904 | 0.096774 | 0.9310345 |
| IL-12p70* | 0.645161 | 0.478464 | 0.551724 | 0.497317 | 0.411491 | 0.301696 | 0.546719 | 0.645161 | 0.4482759 |
| IL-13* | 0.225806 | 0.418112 | 0.344828 | 0.475312 | 0.43659 | 0.272645 | 0.559511 | 0.774194 | 0.3448276 |
| IL-1B* | 0.290323 | 0.453911 | 0.103448 | 0.304543 | 0.411115 | 0.319635 | 0.593437 | 0.290323 | 0.8965517 |
| IL-2* | 0.806452 | 0.395079 | 0.862069 | 0.344828 | 0.354711 | 0.29265 | 0.527809 | 0.193548 | 0.862069 |
| IL-4* | 0.225806 | 0.418112 | 0.241379 | 0.42792 | 0.503227 | 0.289098 | 0.507786 | 0.774194 | 0.2413793 |
| IL-6* | 0.967742 | 0.176685 | 1 | 0 | 0.268862 | 0.208761 | 0.516129 | 0.032258 | 1 |
| ln_Calbindin | 5.465115 | 0.337717 | 5.579209 | 0.318801 | 0.191702 | 0.280814 | 0.598443 | 0.483871 | 0.7241379 |
| ln_CRP | 15.49334 | 1.389378 | 14.84954 | 1.01305 | 0.049643 | 0.201684 | 0.615968 | 0.322581 | 0.9655172 |
| ln_Cytokeratin-8 | 8.843682 | 0.836001 | 8.702134 | 0.732096 | 0.496654 | 0.301052 | 0.543382 | 0.645161 | 0.4827586 |
| ln_Eotaxin | 4.727651 | 0.485403 | 4.834629 | 0.579123 | 0.447852 | 0.298851 | 0.540601 | 0.741935 | 0.4137931 |
| ln_Eotaxin-2 | 7.004298 | 0.787915 | 6.935715 | 0.669992 | 0.723173 | 0.292289 | 0.537264 | 0.580645 | 0.7241379 |
| ln_ICAM-1 | 12.8259 | 0.201037 | 12.95374 | 0.21807 | 0.023707 | 0.162641 | 0.647386 | 0.516129 | 0.7586207 |
| ln_IL-10 | -1.13199 | 0.625707 | -1.02455 | 1.093266 | 0.645116 | 0.29152 | 0.489989 | 0.548387 | 0.5517241 |
| ln_IL-12/IL-23p40 | 4.720552 | 0.557983 | 4.914384 | 0.372711 | 0.127813 | 0.26652 | 0.587875 | 0.483871 | 0.8275862 |
| ln_IL-15 | 1.018222 | 0.272514 | 0.973063 | 0.22097 | 0.492698 | 0.295595 | 0.516685 | 0.580645 | 0.5172414 |
| ln_IL-16 | 5.018129 | 0.494848 | 5.499578 | 0.489007 | 0.000446 | 0.019551 | 0.770587 | 0.645161 | 0.8275862 |
| ln_IL-17A | 0.305611 | 0.590919 | 0.412454 | 0.665443 | 0.519899 | 0.297619 | 0.54505 | 0.290323 | 0.8965517 |
| ln_IL-1a | 1.568199 | 0.858322 | 2.001516 | 1.104647 | 0.099506 | 0.249832 | 0.634594 | 0.83871 | 0.4827586 |
| ln_IL-5 | -1.15946 | 0.916767 | -0.65708 | 0.630306 | 0.018862 | 0.159767 | 0.690211 | 0.548387 | 0.8275862 |
| ln_IL-7 | 1.63682 | 1.039099 | 0.909831 | 0.849293 | 0.005119 | 0.108039 | 0.686318 | 0.612903 | 0.7586207 |
| ln_IL-8 | 1.945043 | 0.614605 | 1.703408 | 0.366981 | 0.076646 | 0.226138 | 0.605673 | 0.258065 | 1 |
| ln_IP-10 | 5.593124 | 0.621223 | 5.752523 | 0.39955 | 0.253412 | 0.297802 | 0.610679 | 0.580645 | 0.6896552 |
| ln_MCP-1 | 4.491126 | 0.329497 | 4.5989 | 0.207386 | 0.144483 | 0.264967 | 0.602336 | 0.580645 | 0.7241379 |
| ln_MCP-2 | 3.222517 | 0.570427 | 2.95958 | 0.451597 | 0.05753 | 0.217044 | 0.62792 | 0.451613 | 0.8965517 |
| ln_MCP-4 | 4.5486 | 0.712429 | 4.126059 | 0.568716 | 0.016046 | 0.151652 | 0.666296 | 0.483871 | 0.8965517 |
| ln_M-CSF | 3.047373 | 0.611555 | 2.505291 | 0.59675 | 0.001177 | 0.068766 | 0.753615 | 0.741935 | 0.7586207 |
| ln_MDC | 6.875199 | 0.413118 | 6.909126 | 0.380924 | 0.746711 | 0.292838 | 0.538932 | 0.290323 | 0.9310345 |
| ln_MIF | 10.77842 | 1.064008 | 10.38574 | 0.823097 | 0.123125 | 0.2638 | 0.617909 | 0.419355 | 0.862069 |
| ln_MIP-1a | 2.728453 | 0.345414 | 2.79287 | 1.040423 | 0.749689 | 0.292168 | 0.47386 | 0.451613 | 0.5862069 |
| ln_MIP-1B | 4.223663 | 0.395755 | 3.949585 | 0.377629 | 0.009204 | 0.147117 | 0.750278 | 0.709677 | 0.7931034 |
| ln_MIP-5 | 8.886618 | 0.249491 | 8.79139 | 0.28901 | 0.183639 | 0.285882 | 0.632369 | 0.709677 | 0.6896552 |
| ln_MMP-1 | 6.996979 | 1.116672 | 7.338659 | 0.715607 | 0.173802 | 0.278738 | 0.590656 | 0.354839 | 1 |
| ln_MMP-3 | 9.004877 | 0.54779 | 9.395839 | 0.40278 | 0.003167 | 0.078774 | 0.718556 | 0.451613 | 0.9655172 |
| ln_MMP-9 | 10.77983 | 0.531793 | 10.89192 | 0.45695 | 0.394246 | 0.306395 | 0.580645 | 0.709677 | 0.5172414 |
| ln_Nectin-4 | 6.940239 | 0.317708 | 6.845671 | 0.27223 | 0.229882 | 0.29508 | 0.61624 | 0.580645 | 0.7586207 |
| ln_Osteoactivin | 9.874019 | 0.235497 | 10.02687 | 0.219122 | 0.013283 | 0.134601 | 0.675195 | 0.387097 | 0.9310345 |
| ln_Osteonectin | 11.42319 | 0.851914 | 11.10696 | 0.632445 | 0.115828 | 0.257069 | 0.580645 | 0.516129 | 0.7586207 |
| ln_P-Cadherin | 9.711695 | 0.345444 | 9.940154 | 0.367756 | 0.017785 | 0.15987 | 0.689655 | 0.806452 | 0.5517241 |

TABLE 3-continued

Biomarker concentrations, p-values and diagnostic ability for each biomarker, including scaled biomarker concentrations

| Biomarker | Seizure Patient Mean | Seizure Standard deviation | Control Mean | Control Standard Deviation | P-value | P val std | AUC | Sensitivity | Specificity |
|---|---|---|---|---|---|---|---|---|---|
| ln_SAA | 15.9064 | 1.447964 | 15.3043 | 0.801467 | 0.057123 | 0.193679 | 0.580089 | 0.290323 | 0.9655172 |
| ln_SCF | 3.662155 | 0.364418 | 3.761249 | 0.257802 | 0.239591 | 0.286835 | 0.572859 | 0.322581 | 0.9310345 |
| ln_TARC | 4.478042 | 1.391039 | 3.909623 | 0.695884 | 0.056315 | 0.218363 | 0.644049 | 0.419355 | 0.9655172 |
| ln_TNF-RI | 7.691596 | 0.262475 | 7.656299 | 0.302514 | 0.636253 | 0.301906 | 0.577864 | 0.741935 | 0.4137931 |
| ln_TNF-RII | 8.144642 | 0.315924 | 8.136595 | 0.367319 | 0.928903 | 0.291369 | 0.486096 | 0.225806 | 0.7931034 |
| ln_TNF-a | 0.709647 | 0.53049 | 1.008034 | 0.314674 | 0.012334 | 0.117456 | 0.692436 | 0.419355 | 0.9655172 |
| ln_TNF-B | -1.82692 | 0.813754 | -1.47361 | 0.387548 | 0.041207 | 0.177808 | 0.632369 | 0.774194 | 0.5517241 |
| ln_TRAIL | 5.290881 | 0.487545 | 5.675706 | 0.347042 | 0.001077 | 0.045043 | 0.739711 | 0.709677 | 0.7586207 |
| ln_VCAM-1 | 13.24795 | 0.286811 | 13.20666 | 0.212458 | 0.537946 | 0.301639 | 0.584538 | 0.580645 | 0.6551724 |
| ln_VEGF-A | 3.981521 | 0.682258 | 4.032727 | 0.729284 | 0.783321 | 0.293047 | 0.496663 | 0.096774 | 0.9655172 |

*indicates biomarkers that were used as binary classifiers of detectable levels
**all values reported in pg/mL, except binary classificiers Example 2: Diagnostic Capacity of Biomarker Interactions Diagnostic capacity of biomarker interactions and performance of all biomarkers are shown in Table 4.

Example 3: Examples of Diagnostic Algorithms for all Combinations of Two Biomarkers Examples of diagnostic algorithms for all combinations of two biomarkers are shown in Table 5.

Example 4: Examples of Diagnostic Algorithms for all Combinations of Three Biomarkers Examples of diagnostic algorithms for all combinations of five biomarkers are shown in Table 6.

Example 5: Examples of Diagnostic Algorithms for all Combinations of Five Biomarkers Examples of diagnostic algorithms for all combinations of five biomarkers are shown in Table 7.

Example 6: Examples of Diagnostic Algorithms for all Combinations of Five Biomarkers, where TARC is Included Examples of diagnostic algorithms for all combinations of five biomarkers where TARC is included, are shown in Table 8.

Example 7: Examples of Diagnostic Algorithms for all Combinations of Five Biomarkers, where TARC and TNF-α are Included Examples of diagnostic algorithms for all combinations of five biomarkers, where TARC and TNF-α are included, are shown in Table 9.

Figure 3:
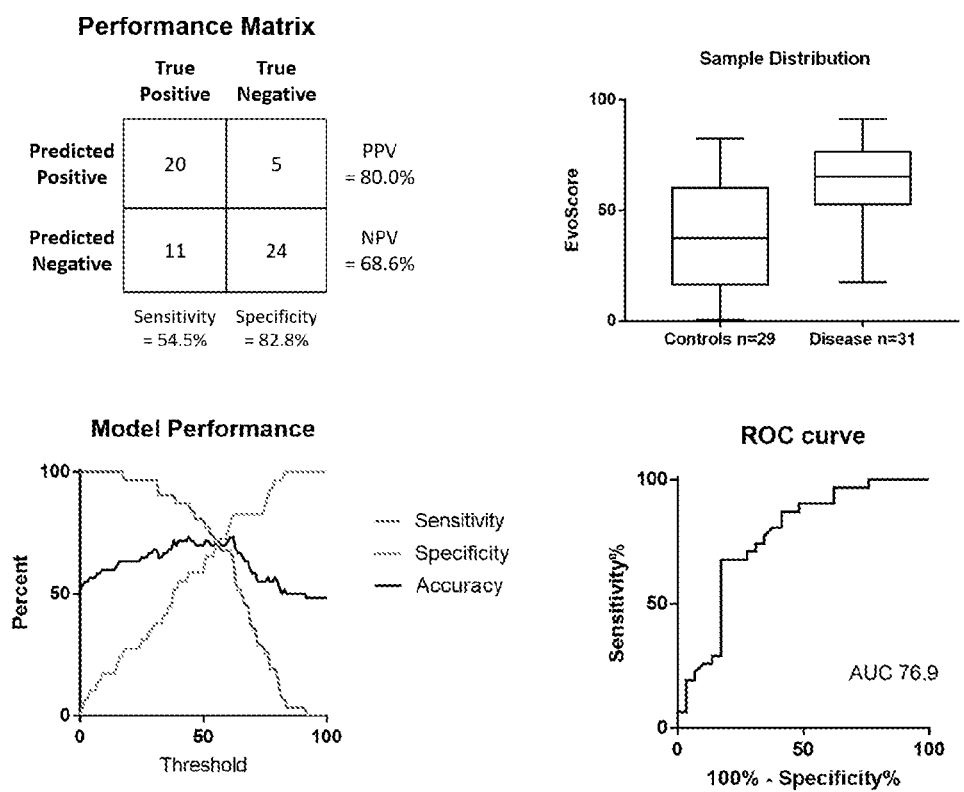
FIG. 3 illustrates an example of Using 1 biomarkers for an algorithm with IL-16.
Figure 4:
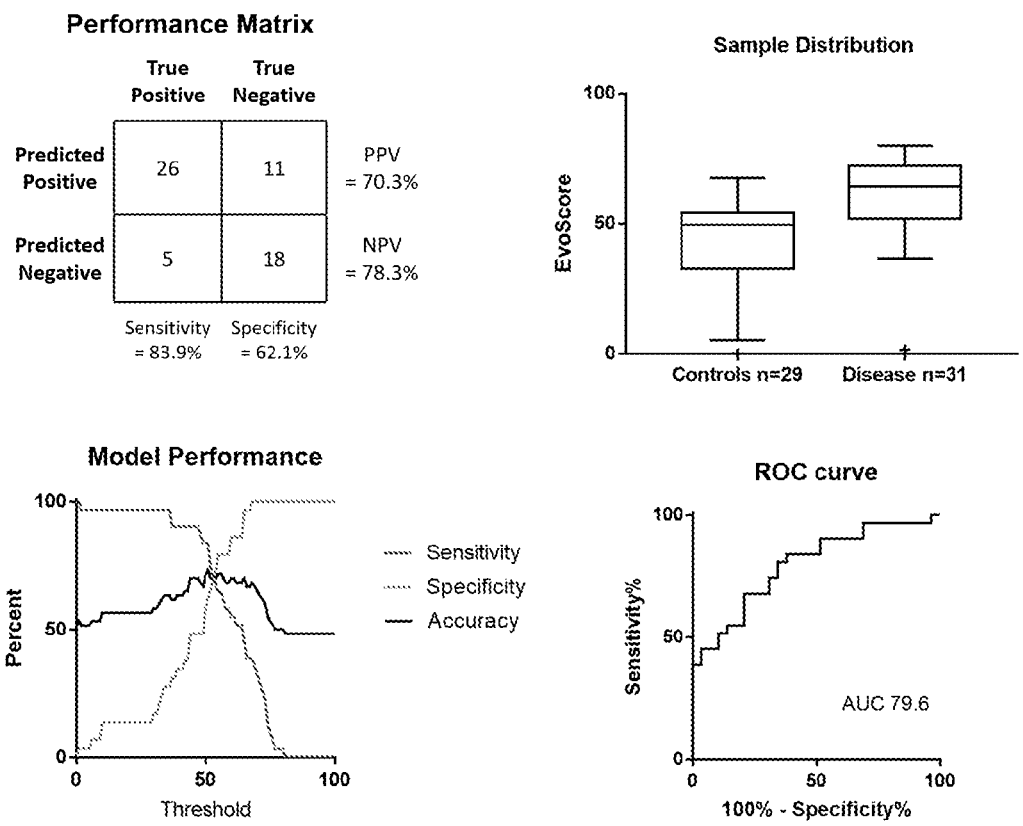
FIG. 4 illustrates an example of using biomarker products for an algorithm with MMP-3 and TNFa.
Figure 5:
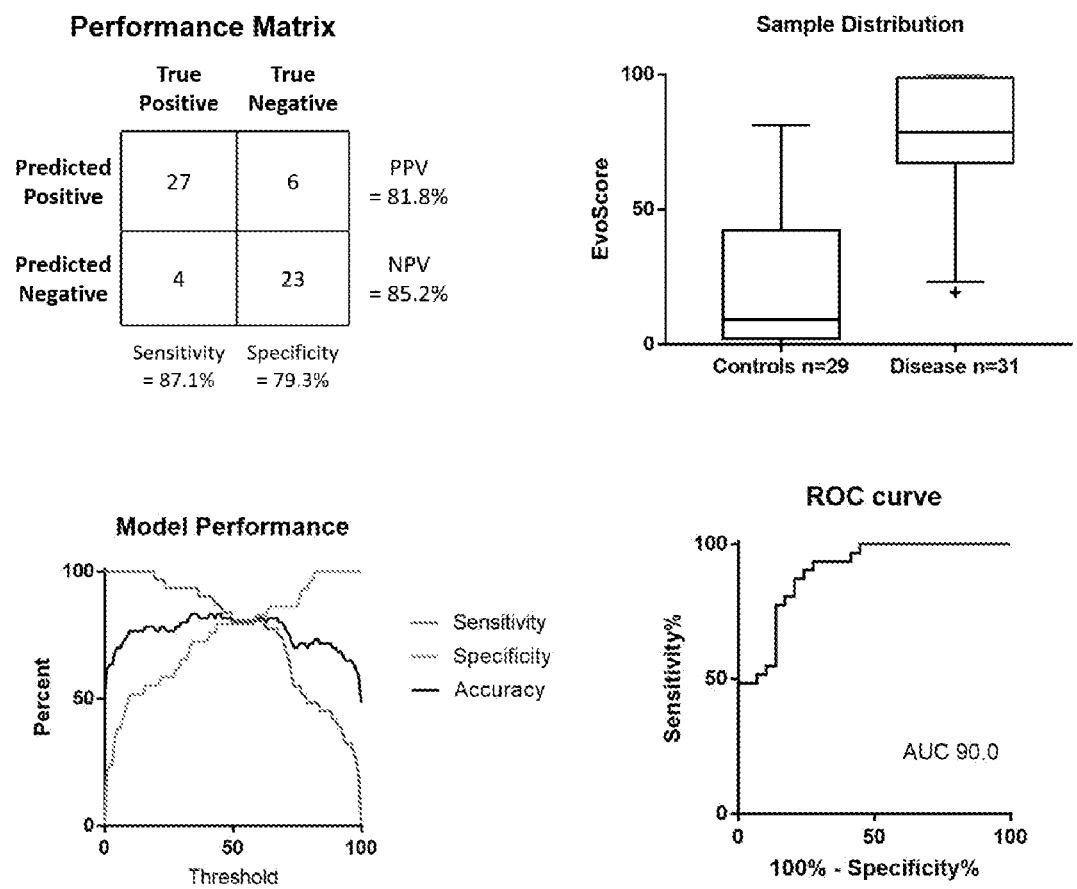
FIG. 5 illustrates an example of Using 2 biomarkers for an algorithm with TARC and IL-16.
Figure 6:
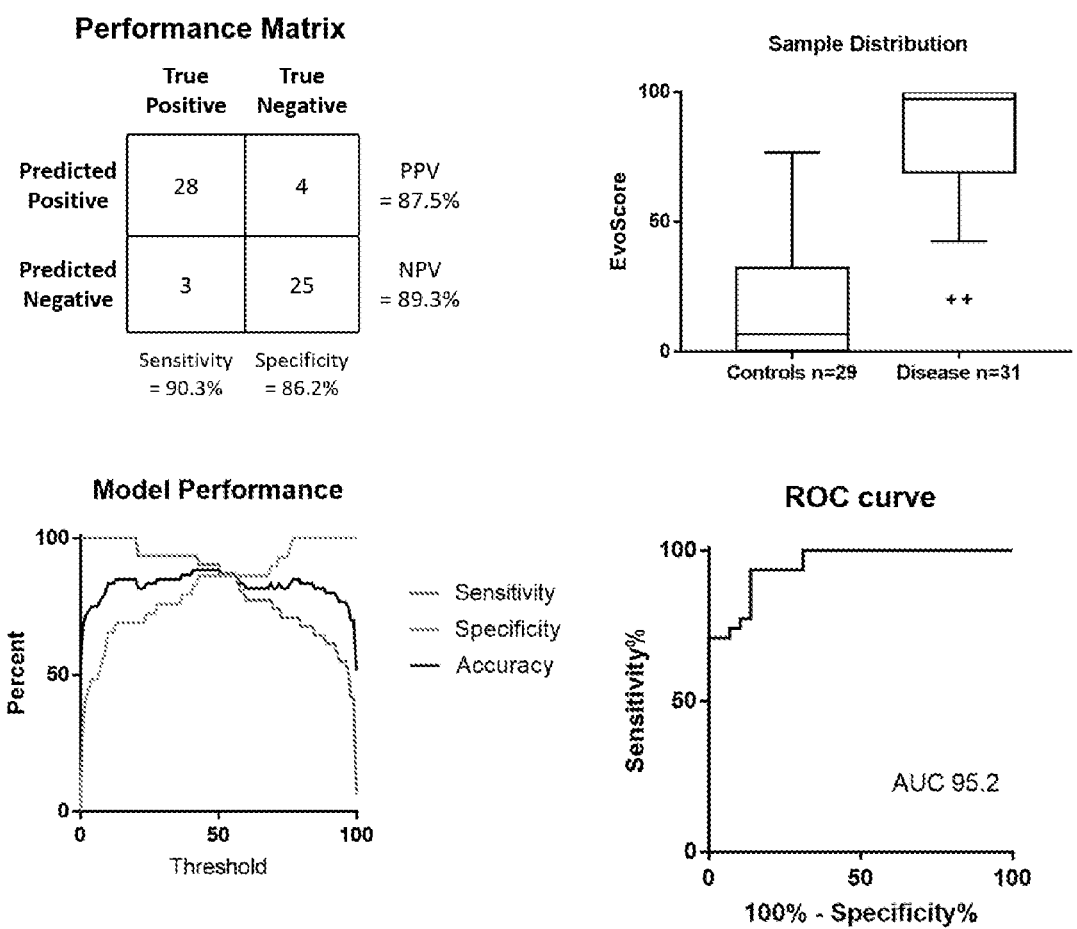
FIG. 6 illustrates an example of Using 3 biomarkers for an algorithm with TARC, IL-16, and SAA.
Figure 7:
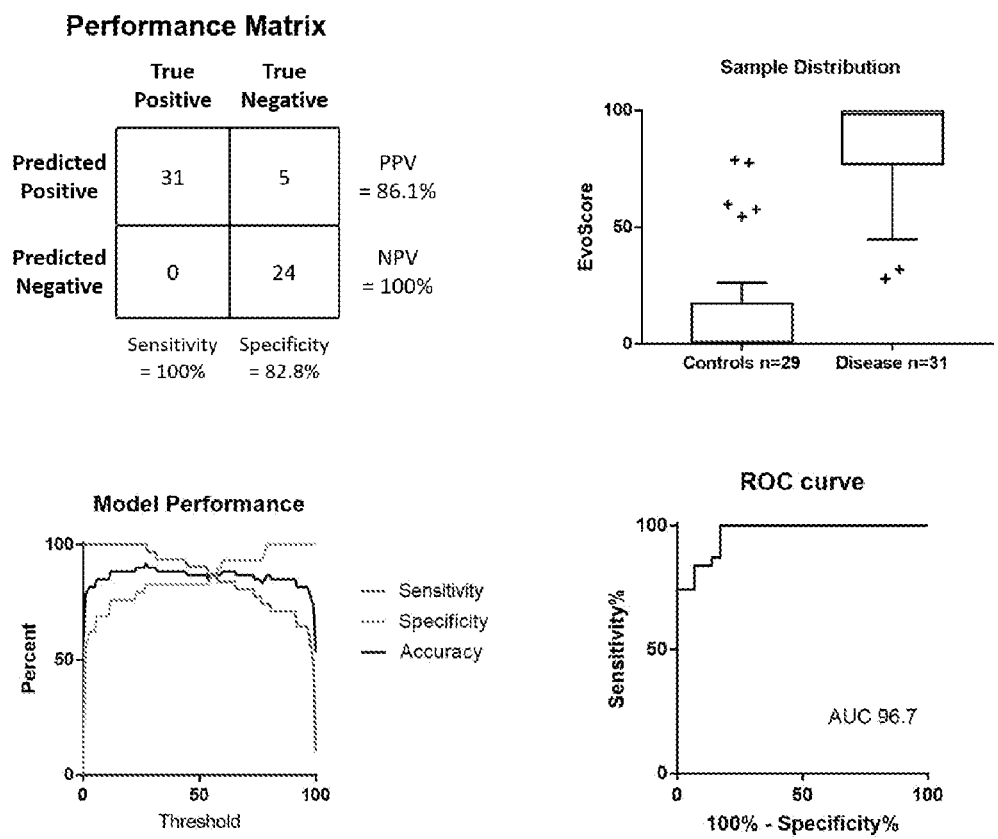
FIG. 7 illustrates an example of using 5 biomarkers for an algorithm Including TARC, IL-16, SAA, M-CSF, and MCP-4.
Figure 8:
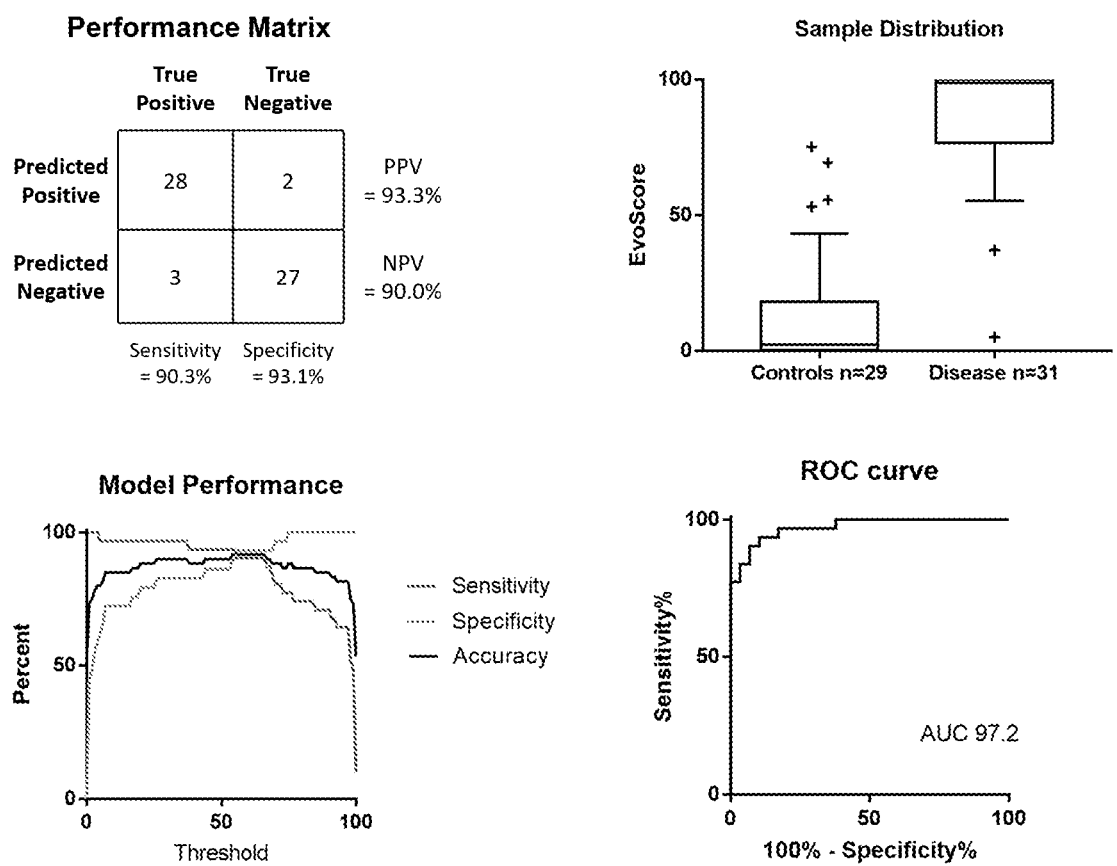
FIG. 8 illustrates an example of using 5 biomarkers including TARC, TNFa, Nectin-4, IL-16, and SAA.
Figure 9:
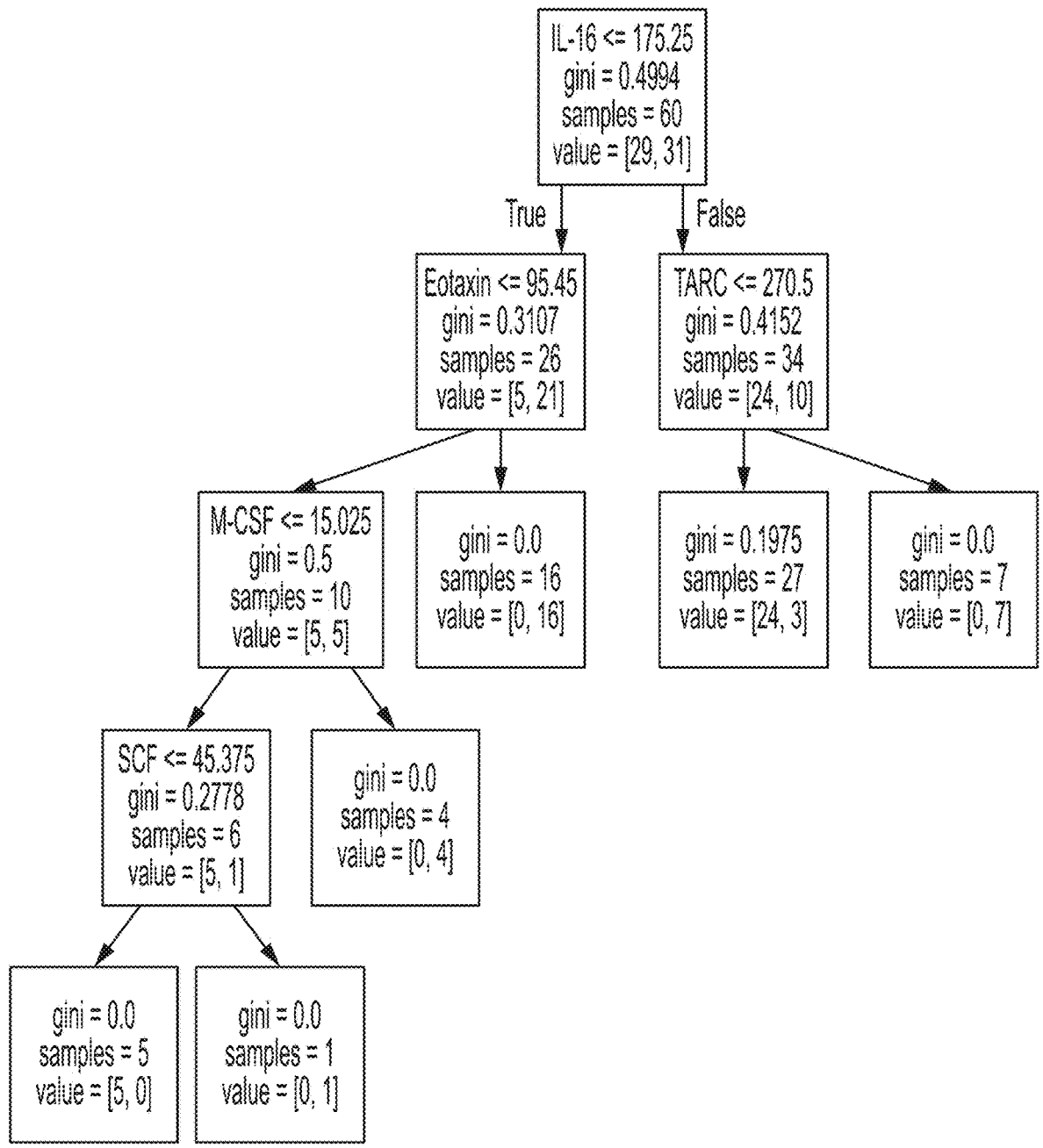
FIG. 9 illustrates an example of using a classification tree to predict seizure-biomarker concentrations.
Figure 10:
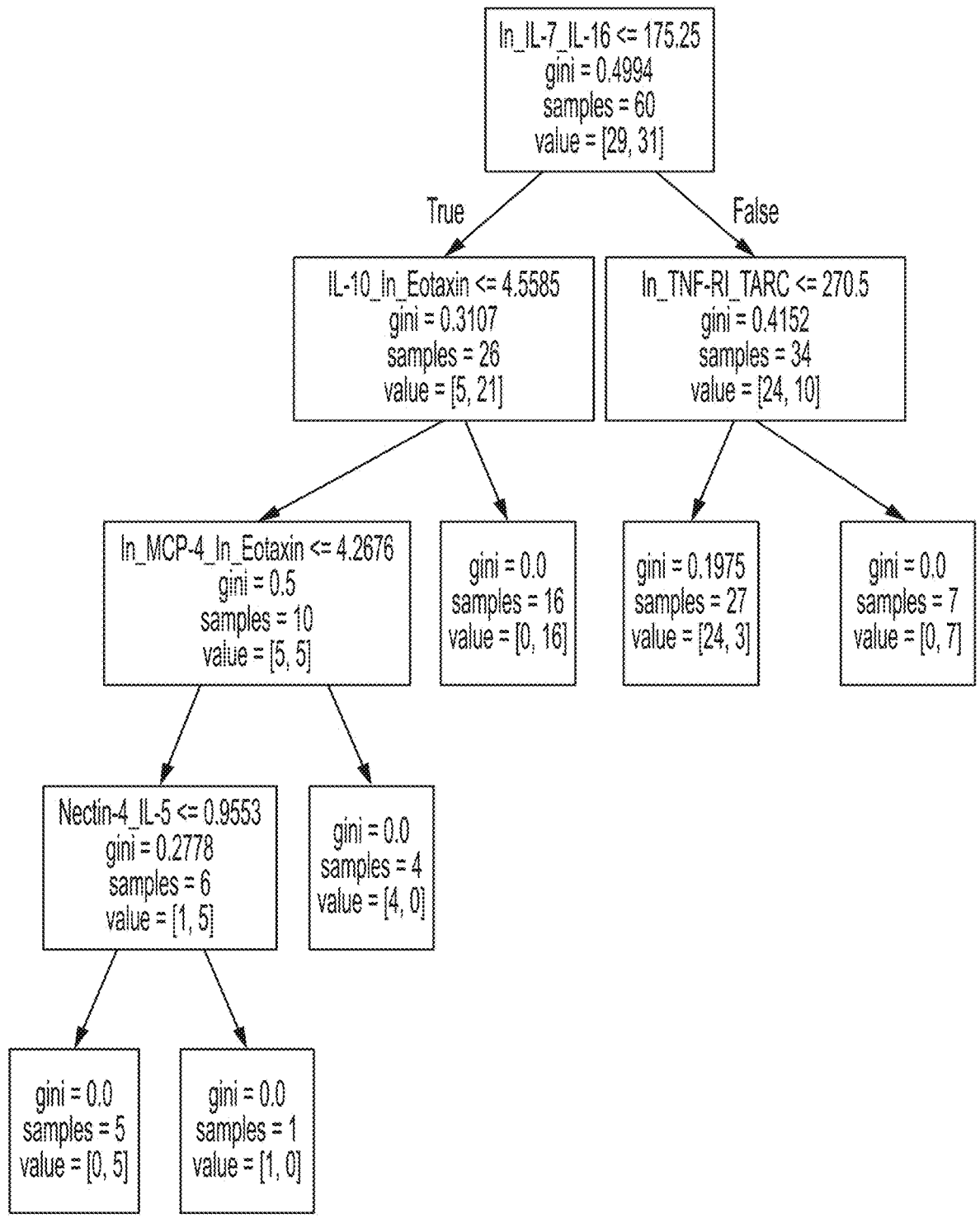
FIG. 10 illustrates an example of using a classification tree to predict seizure-using products of scaled biomarkers.
Figure 11:
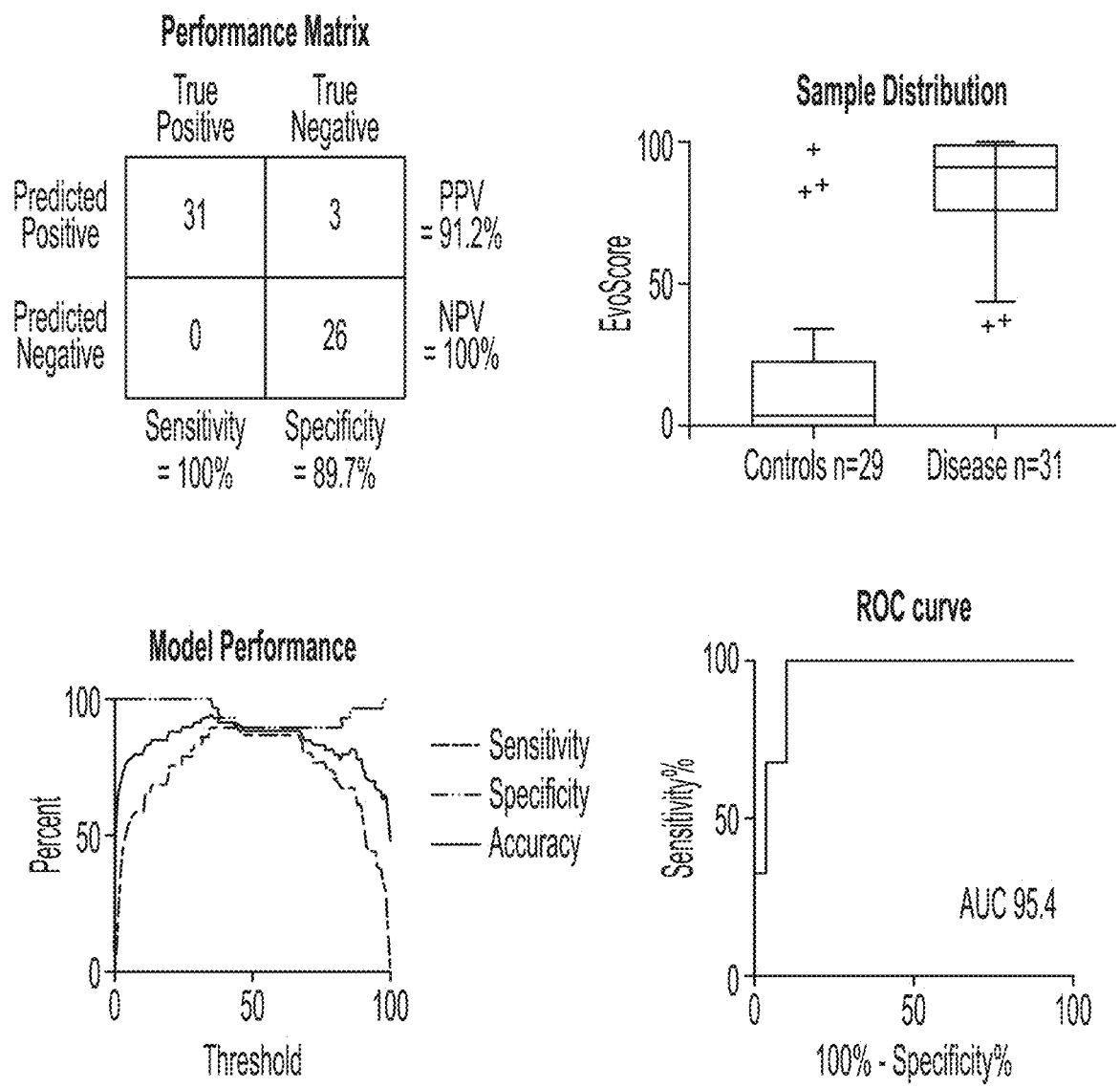
FIG. 11 illustrates an example of using 7 biomarkers in an algorithm, including IL-16, TARC, TNF-α, MIP-1B, TRAIL, MMP-3, P-Cadherin.

Example 8: Detailed Diagnostic Parameters for Multiple Algorithms for One or More Biomarkers FIG. 3 illustrates an example of Using 1 biomarkers for an algorithm with IL-16.
FIG. 4 illustrates an example of using biomarker products for an algorithm with MMP-3 and TNFa.
FIG. 5 illustrates an example of Using 2 biomarkers for an algorithm with TARC and IL-16.
FIG. 6 illustrates an example of Using 3 biomarkers for an algorithm with TARC, IL-16, and SAA
FIG. 7 illustrates an example of using 5 biomarkers for an algorithm Including TARC, IL-16, SAA, M-CSF, and MCP-4.
FIG. 8 illustrates an example of using 5 biomarkers including TARC, TNFa, Nectin-4, IL-16, and SAA
FIG. 11 illustrates an example of using 7 biomarkers in an algorithm, including IL-16, TARC, TNF-α, MIP-1B, TRAIL, MMP-3, P-Cadherin Example 9: Detailed Diagnostic Parameters for Multiple Algorithms for One or More Biomarkers Leveraging Classification Trees FIG. 9 illustrates an example of using a classification tree to predict seizure-biomarker concentrations.
FIG. 10 illustrates an example of Using a classification tree to predict seizure—using products of scaled biomarkers.

Example 10: EEG and EvoScore

EEG was demonstrated to have a Sensitivity of 37%, Specificity of 99%, PPV of 98%, and NPV of 66%. We found that EEG may miss seizure events, resulting in significant false negatives and corresponding potential under-treatment of epilepsy patients. Our results are reflective of the recognized range of this test (Sensitivity of 25-56%, and Specificity of 78%-98%). EvoScore demonstrated better sensitivity and negative predictive value, and near equivalent specificity and positive predictive value when evaluating phasic changes versus EEG.

EvoScore can be used in combination with EEG for patient diagnosis and treatment. Additionally, EvoScore can be used in combination with other diagnostic and test approaches as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The mathematical coefficients and algorithms provided herein are illustrative and exemplary and are provided for the purpose of illustration only, in order to demonstrate the effectiveness of leveraging one or more biomarkers in multiple potential diagnostic algorithms with performance to meet diagnostic needs. The disclosure encompassed herein should in no way be construed as being limited to these examples of coefficients and algorithms, but rather should be construed to encompass any and all variations which become evident as a result of the teachings provided herein. In particular, alternative coefficients and algorithms may become apparent as a result of the use of different clinical data.

Although the invention has been described in conjunction with specific embodiments thereof, it is evident that many alternatives, modification and variations will be apparent to those skilled in the art. Accordingly, it is intended to embrace all such alternatives, modification and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Any document (including but not limited to any patent, patent application, publication, and website) listed herein is hereby incorporated herein by reference in its entirety. While these developments have been disclosed with reference to specific embodiments, it is apparent that other embodiments and variations of this invention are devised by others skilled in the art without departing from the true spirit and scope of the developments. The appended claims include such embodiments and variations thereof.

What is claimed is:

1. A method of treating epilepsy in a patient in need of epilepsy treatment, the method comprising:
    contacting one or more blood samples obtained from the patient with one or more antibodies targeting one or more biomarkers selected from the group consisting of thymus and activation-regulated chemokine (TARC), interleukin (IL)-7, monocyte chemotactic protein (MCP)-4, macrophage colony-stimulating factor (M-CSF), MCP-2, IL-8, macrophage inflammatory protein (MIP)-1B, macrophage migration inhibitory factor (MIF), Eotaxin, MIP-5, IL-15, Eotaxin-2, TNF-RI, interferon gamma-induced protein 10 (IP-10), granulocyte macrophage colony stimulating factor (GM-CSF), IL-12p70, and IL-1B;
    measuring the concentrations of the one or more biomarkers in the one or more blood samples;
    comparing the concentrations of the one or more biomarkers in the one or more blood samples to the concentration of the one or more biomarkers in one or more controls; and
    treating the patient for epilepsy by administering to the patient one or more therapeutic agents selected from the group consisting of phenytoin, carbamazepine, oxcarbazepine, zonisamide, lamotrigine, and pharmaceutically acceptable salts and prodrugs thereof;
    wherein the patient is in need of epilepsy treatment when the concentrations of the one or more biomarkers are elevated in the one or more blood samples relative to the one or more controls.

2. The method of claim 1, wherein the one or more biomarkers is thymus and activation-regulated chemokine (TARC).

3. The method of claim 1, wherein the patient has suffered one or more seizures.

4. A method of treating epilepsy in a patient having an elevated blood level of one or more biomarkers selected from the group consisting of thymus and activation-regulated chemokine (TARC), interleukin (IL)-7, monocyte chemotactic protein (MCP)-4, macrophage colony-stimulating factor (M-CSF), MCP-2, IL-8, macrophage inflammatory protein (MIP)-1B, macrophage migration inhibitory factor (MIF), Eotaxin, MIP-5, IL-15, Eotaxin-2, TNF-RI, interferon gamma-induced protein 10 (IP-10), granulocyte macrophage colony stimulating factor (GM-CSF), IL-12p70, and IL-1B; the method comprising administering to the patient one or more therapeutic agents selected from the group consisting of phenytoin, carbamazepine, lamotrigine, oxcarbazepine, zonisamide, and pharmaceutically acceptable salts and prodrugs thereof.

5. The method of claim 4, wherein the patient has suffered one or more seizures.

6. A method of treating epilepsy in a patient in need of epilepsy treatment, the method comprising:
    contacting one or more blood samples obtained from the patient with one or more antibodies targeting one or more biomarkers selected from the group consisting of interleukin-16 (IL-16), tumor necrosis factor-related apoptosis-inducing ligand (TRAIL), tumor necrosis factor (TNF)-α, IL-5, tumor necrosis factor-beta (TNF-β), MCP-1, interleukin-10 (IL-10), MIP-1a, IL-12/IL-23p40, IL-17A, stem cell factor (SCF), IL-1a, macrophage derived chemokine (MDC), TNF-RII, Eotaxin-3, interferon-gamma (IFN-γ), IL-13, IL-2, IL-4, and IL-6;
    measuring the concentrations of the one or more biomarkers in the one or more blood samples; comparing the concentrations of the one or more biomarkers in the one or more blood samples to the concentration of the one or more biomarkers in one or more controls; and
    treating the patient for epilepsy by administering to the patient one or more therapeutic agents selected from the group consisting of phenytoin, carbamazepine, oxcarbazepine, zonisamide, lamotrigine, and pharmaceutically acceptable salts and prodrugs thereof;
    wherein the patient is in need of epilepsy treatment when the concentrations of the one or more biomarkers are decreased in the one or more blood samples relative to the one or more controls.

7. The method of claim 6, wherein the one biomarker is IL-16.

8. The method of claim 6, wherein the one or more biomarkers are IL-16 and TNF-α.

9. A method of treating epilepsy in a patient having an decreased blood level of one or more biomarkers selected from the group consisting of: interleukin-16 (IL-16), tumor necrosis factor-related apoptosis-inducing ligand (TRAIL), tumor necrosis factor (TNF)-α, IL-5, tumor necrosis factor-beta (TNF-β), MCP-1, interleukin-10 (IL-10), MIP-1a, IL-12/IL-23p40, IL-17A, stem cell factor (SCF), IL-1a, macrophage derived chemokine (MDC), TNF-RII, Eotaxin-3, interferon-gamma (IFN-γ), IL-13, IL-2, IL-4, and IL-6; the method comprising administering to the patient one or more therapeutic agents selected from the group consisting of phenytoin, carbamazepine, lamotrigine, oxcarbazepine, zonisamide, and pharmaceutically acceptable salts and prodrugs thereof.

10. The method of claim 9, wherein the one biomarker is IL-16.

11. The method of claim 9, wherein the one or more biomarkers are IL-16 and TNF-α.

* * * * *